(12) United States Patent
Wang et al.

(10) Patent No.: US 12,138,274 B2
(45) Date of Patent: Nov. 12, 2024

(54) COMPOSITIONS AND METHODS FOR THE TREATMENT OF PERIPHERAL ARTERY DISEASE AND CARDIOPULMONARY DISEASES

(71) Applicant: BOARD OF REGENTS OF THE UNIVERSITY OF NEBRASKA, Lincoln, NE (US)

(72) Inventors: Hanjun Wang, Omaha, NE (US); Dong Wang, Omaha, NE (US); Thomas Nicholas, Omaha, NE (US); Michael Lankhorst, Elkhorn, NE (US); Steven Lisco, Omaha, NE (US); Irving Zucker, Omaha, NE (US); Lie Gao, Omaha, NE (US); Juan Hong, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 812 days.

(21) Appl. No.: 17/290,912

(22) PCT Filed: Nov. 8, 2019

(86) PCT No.: PCT/US2019/060439
§ 371 (c)(1),
(2) Date: May 3, 2021

(87) PCT Pub. No.: WO2020/097442
PCT Pub. Date: May 14, 2020

(65) Prior Publication Data
US 2021/0386764 A1 Dec. 16, 2021

Related U.S. Application Data

(60) Provisional application No. 62/757,406, filed on Nov. 8, 2018, provisional application No. 62/757,410, filed on Nov. 8, 2018.

(51) Int. Cl.
| A61K 31/65 | (2006.01) |
| A61K 9/00 | (2006.01) |
| A61K 31/573 | (2006.01) |
| A61K 45/06 | (2006.01) |
| A61P 9/14 | (2006.01) |

(52) U.S. Cl.
CPC ............ *A61K 31/65* (2013.01); *A61K 9/0019* (2013.01); *A61K 31/573* (2013.01); *A61K 45/06* (2013.01); *A61P 9/14* (2018.01)

(58) Field of Classification Search
CPC ...... A61K 31/65; A61K 9/0019; A61K 45/06; A61P 9/00; A61P 9/10; A61P 9/14
See application file for complete search history.

(56) References Cited

U.S. PATENT DOCUMENTS

| 10,092,662 | B2 | 10/2018 | Wang et al. |
| 2008/0051454 | A1 | 2/2008 | Wang |
| 2010/0113406 | A1* | 5/2010 | Hermans ............... A61K 31/573 |
| | | | 514/178 |
| 2010/0292183 | A1 | 11/2010 | Madasamy |
| 2012/0172429 | A1 | 7/2012 | Woolf et al. |
| 2014/0296255 | A1 | 10/2014 | Maes et al. |
| 2015/0080460 | A1 | 3/2015 | Zucker et al. |
| 2015/0141959 | A1 | 5/2015 | Seward |

FOREIGN PATENT DOCUMENTS

| WO | 00/16783 | A1 | 3/2000 |
| WO | 02/072103 | A1 | 9/2002 |
| WO | 2005/013948 | A2 | 2/2005 |
| WO | 2008/115441 | A1 | 9/2008 |
| WO | 2015160842 | A1 | 10/2015 |
| WO | 2015160843 | A1 | 10/2015 |
| WO | 2017/080919 | A1 | 5/2017 |
| WO | 2017/139487 | A1 | 8/2017 |
| WO | 2018/148523 | A1 | 8/2018 |

OTHER PUBLICATIONS

Mayo Clinic, Peripheral Artery Disease, last updated Jul. 17, 2018 (accessed via the Wayback Machine on Mar. 5, 2024 _. (Year: 2018).*
Xing, J.; et al. "Role of TNF-a in Regulating the Exercise Pressor Reflex in Rats With Femoral Artery Occlusion" 2018, Frontiers in Physiology, vol. 9, art. 1461. (published Oct. 15, 2018. (Year: 2018).*
Kwon, M.J.; et al. "Contribution of Macrophages to Enhanced Regenerative Capacity of Dorsal Root Ganglia Sensory Neurons by Conditioning Injury" 2013, The Journal of Neuroscience, vol. 33, pp. 15095-15108 (Year: 2013).*
Li, J.-Y.; et al. "Mechanical Hypersensitivity, Sympathetic Sprouting, and Glial Activation Are Attenuated by Local Injection of Corticosteroid Near the Lumbar Ganglion in a Rat Model of Neuropathic Pain" Regional Anesthesia and Pain Medicine 2011, vol. 36, pp. 56-62. (Year: 2011).*
Liang, L.; et al. "The Phosphodiesterase Inhibitors Pentoxifylline and Rolipram Prevent Diabetes in NOD Mice" 1998, Diabetes, vol. 47, pp. 570-575. (Year: 1998).*
Cortijo, et al., "Roflumilast, a phosphodiesterase 4 inhibitor, alleviates bleomycin-induced lung injury" Br. J. Pharmacol. (2009) 156(3):534-44.
Hu, et al., "Minocycline attenuates ischemia-induced ventricular arrhythmias in rats" Eur. J. Pharmacol. (2011) 654(3):274-9.

(Continued)

*Primary Examiner* — Eric Olson
*Assistant Examiner* — Benjamin M Brandsen
(74) *Attorney, Agent, or Firm* — Robert C. Netter, Jr.; Dann, Dorfman, Herrell & Skillman

(57) ABSTRACT

Compositions and methods for the treatment of peripheral artery disease and cardiopulmonary diseases or disorders are provided. In accordance with the instant invention, methods of inhibiting, treating, and/or preventing peripheral artery disease or symptoms associated therewith are provided. In a particular embodiment, the methods inhibit, treat, and/or prevent claudication associated with peripheral artery disease.

23 Claims, 14 Drawing Sheets

(56) References Cited

OTHER PUBLICATIONS

Figure 1:
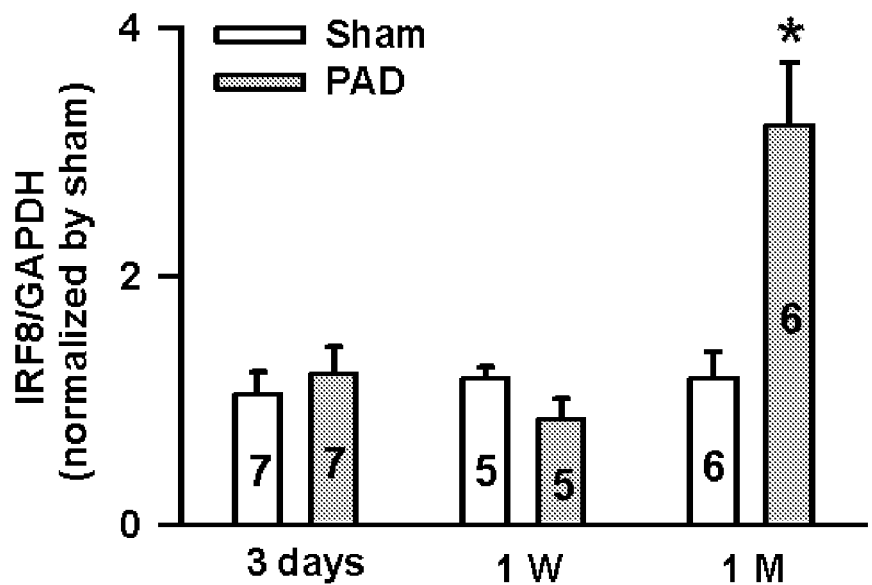

Bonjoch, et al., "Minocycline inhibits peritoneal macrophages but activates alveolar macrophages in acute pancreatitis" J. Physiol. Biochem. (2015) 71(4):839-46.

Zhao, et al., "Minocycline improves cardiac function after myocardial infarction in rats by inhibiting activation of PARP-1" Biomed. Pharmacother. (2018) 97:1119-1124.

Schiller, et al., "Increased Brain-Derived Neurotrophic Factor in Lumbar Dorsal Root Ganglia Contributes to the Enhanced Exercise Pressor Reflex in Heart Failure" Int. J. Mol. Sci. (2019) 20:1480.

Shanks, et al., "TRPV1 (Transient Receptor Potential Vanilloid 1) Cardiac Spinal Afferents Contribute to Hypertension in Spontaneous Hypertensive Rat" Hypertension (2019) 74:910-920.

Shanks, et al., "Sympatho-excitatory response to pulmonary chemosensitive spinal afferent activation in anesthetized, vagotomized rats" Physiol. Rep. (2018) 6(12):e13742.

Caterina, M.J., et al., "The capsaicin receptor: a heat-activated ion channel in the pain pathway" Nature (1997) 389(6653):816-24.

Wu, et al., "Roles of peripheral terminals of transient receptor potential vanilloid-1 containing sensory fibers in spinal cord stimulation-induced peripheral vasodilation" Brain Res. (2007) 1156:80-92.

Li, et al., "Muscle afferent receptors engaged in augmented sympathetic responsiveness in peripheral artery disease" Front. Physiol. (2012) 3:247.

Wang, et al., "Thoracic Epidural Administration of Resiniferatoxin Improves Cardiac and Autonomic Dysfunction in Post-MI Rats" Hypertension (2015) 66(suppl 1):Abstract P216.

Short, et al., "Orally-administered TRPV1 and TRPA1 activators inhibit electrically-induced muscle cramps in normal healthy volunteers (S17.003)" Neurology (2015) 84(14 Supplement):S17.003.

Sutherland, et al., "TRPV1 and TRPA1 Activators Demonstrate Efficacy on Human Muscle Cramping. Potential New Treatment for MS Muscle Cramps and Spasticity" (2016) ACTRIMS Forum, New Orleans, Lousiana, Feb. 18-20, 2016.

Short, et al., "Chemical Neuro Stimulation by FLX-787, a co-activator of TRPA1/TRPV1, for the Potential Treatment of Cramps, Spasms and Spasticity (P5.112)" Neurology (2017) 88(16 Supplement):P5.112.

Short, et al., "537.15 Chemical Neuro Stimulation of the upper alimentary canal by TRPV1 and TRPA1 activation decreases muscle cramp frequency and severity" Society for Neuroscience Annual Meeting, San Diego, CA, (Nov. 12, 2016).

Rosen, et al., "Synthetic TRP Activators Demonstrate Efficacy in Preventing Human Muscle Cramping: Potential New Drug Treatment for Muscle Cramps and Spasticity (P2.275)" Neurology (2016) 86(16_supplement):P2.275.

Leo, et al., "Intrathecal resiniferatoxin modulates TRPV1 in DRG neurons and reduces TNF-induced pain-related behavior" Mediators Inflamm. (2017) 2017:2786427.

Yu, et al., "The role of TRPVl in different subtypes of dorsal root ganglion neurons in rat chronic inflammatory nociception induced by complete Freund's adjuvant" Mol. Pain (2008) 4:61.

* cited by examiner

COMPOSITIONS AND METHODS FOR THE TREATMENT OF PERIPHERAL ARTERY DISEASE AND CARDIOPULMONARY DISEASES

This application is a § 371 application of PCT/US2019/060439, filed Nov. 8, 2019, which claims priority under 35 U.S.C. § 119 (e) to U.S. Provisional Patent Application No. 62/757,406, filed on Nov. 8, 2018, and U.S. Provisional Patent Application No. 62/757,410, filed on Nov. 8, 2018. The foregoing applications are incorporated by reference herein.

FIELD OF THE INVENTION

This invention relates generally to the field of cardiovascular and lung diseases. Specifically, the invention provides compositions and methods for the treatment of peripheral artery disease and cardiopulmonary diseases or disorders.

BACKGROUND OF THE INVENTION

Peripheral artery disease (PAD) is a manifestation of systemic atherosclerosis affecting around 8 to 12 million people in the United States, most of them elderly. Symptoms of PAD include claudication, resting pain, and tissue loss which are all consequences of skeletal myopathy and skeletal muscle sensory dysfunction. The exercise pressor reflex (EPR) is a neural reflex originating in skeletal muscle that contributes to the regulation of the cardiovascular and respiratory systems during physical activity. The sensory arm of this reflex is composed of both metabolically sensitive (group IV) and mechanically sensitive (group III) nerves. Evidence from human and animal studies has demonstrated that increases in heart rate (HR), arterial pressure (AP) and sympathetic nerve activity in response to activation of this reflex are enhanced in PAD patients and animals, indicating that an exaggerated EPR exists in the PAD state. The exaggerated EPR can cause a potent vasoconstriction and limit blood flow to exercising muscle, which can contribute to the symptom of exercise intolerance in the PAD patients. Indeed, intermittent claudication (e.g., exercise-induced leg pain and severe walking limitation) is a hallmark of PAD which severely limits exercise capacity and deceases quality of life. Only 5% of PAD patients with claudication receive revascularization. Improved therapeutics for treating PAD and the symptoms associated therewith are needed.

SUMMARY OF THE INVENTION

In accordance with the instant invention, methods of inhibiting, treating, and/or preventing peripheral artery disease or symptoms associated therewith are provided. In a particular embodiment, the methods inhibit, treat, and/or prevent claudication associated with peripheral artery disease. In a particular embodiment, the method improves the exercise performance of the subject. Compositions for use in these methods are also provided. In a particular embodiment, the subject being treated by the methods of the instant invention has an ankle-brachial index ratio less than 0.9, less than 0.8, less than 0.7, less than 0.6, or less than 0.5.

In a particular embodiment, the methods comprise administering an inhibitor or macrophage activation and/or activity. In a particular embodiment, the macrophage inhibitor is a tetracycline such as minocycline, doxycycline, etc. In a particular embodiment, the macrophage inhibitor is a glucocorticoid (e.g., dexamethasone) or a prodrug thereof (e.g., P-Dex and analogs and/or derivatives thereof). In a particular embodiment, the methods comprise administering the macrophage inhibitor by intrathecal administration, epidural administration, or intraganglionic administration. In a particular embodiment, the macrophage inhibitor is administered within the lumbar dorsal root ganglion, particularly at one or more of the lumbar regions L4-L6 (e.g., via an epidural injection). The methods of the instant invention may further comprise administering at least one other therapeutic for the treatment of peripheral artery disease and/or a symptom thereof. The methods of the instant invention may further comprise diagnosing peripheral artery disease in the subject prior to administration of the therapy.

In accordance with another aspect of the instant invention, methods of inhibiting, treating, and/or preventing a cardiopulmonary disease or disorder, acute or chronic heart or lung injury, and/or symptoms associated therewith are provided. In a particular embodiment, the methods inhibit, treat, and/or prevent an acute heart injury and/or symptoms associated thereof. In a particular embodiment, the methods inhibit, treat, and/or prevent a myocardial infarction and/or symptoms associated thereof. In a particular embodiment, the methods inhibit, treat, and/or prevent pulmonary fibrosis and/or symptoms associated thereof. Compositions for use in these methods are also provided.

In a particular embodiment, the methods comprise administering an inhibitor or macrophage activation and/or activity. In a particular embodiment, the macrophage inhibitor is a tetracycline such as minocycline, doxycycline, etc. In a particular embodiment, the macrophage inhibitor is a glucocorticoid (e.g., dexamethasone) or a prodrug thereof (e.g., P-Dex and analogs and/or derivatives thereof). In a particular embodiment, the methods comprise administering the macrophage inhibitor by intrathecal administration, epidural administration, or intraganglionic administration. In a particular embodiment, the macrophage inhibitor is administered within the thoracic dorsal root ganglion, particularly at one or more of the thoracic regions T1-T4 (e.g., via an epidural injection). The methods of the instant invention may further comprise administering at least one other therapeutic for the treatment of a cardiopulmonary disease or disorder, acute or chronic heart or lung injury, and/or symptoms associated therewith. The methods of the instant invention may further comprise diagnosing a cardiopulmonary disease or disorder and/or acute or chronic heart or lung injury in the subject prior to administration of the therapy.

BRIEF DESCRIPTIONS OF THE DRAWING

FIG. 1 provides a graph of Interferon Regulatory Factor 8 (IRF8) expression in healthy sham-treated rats or PAD rats at the indicated times. Mean±standard error (SE). Number of rats indicated. * P<0.05 vs. sham.

Figure 2:
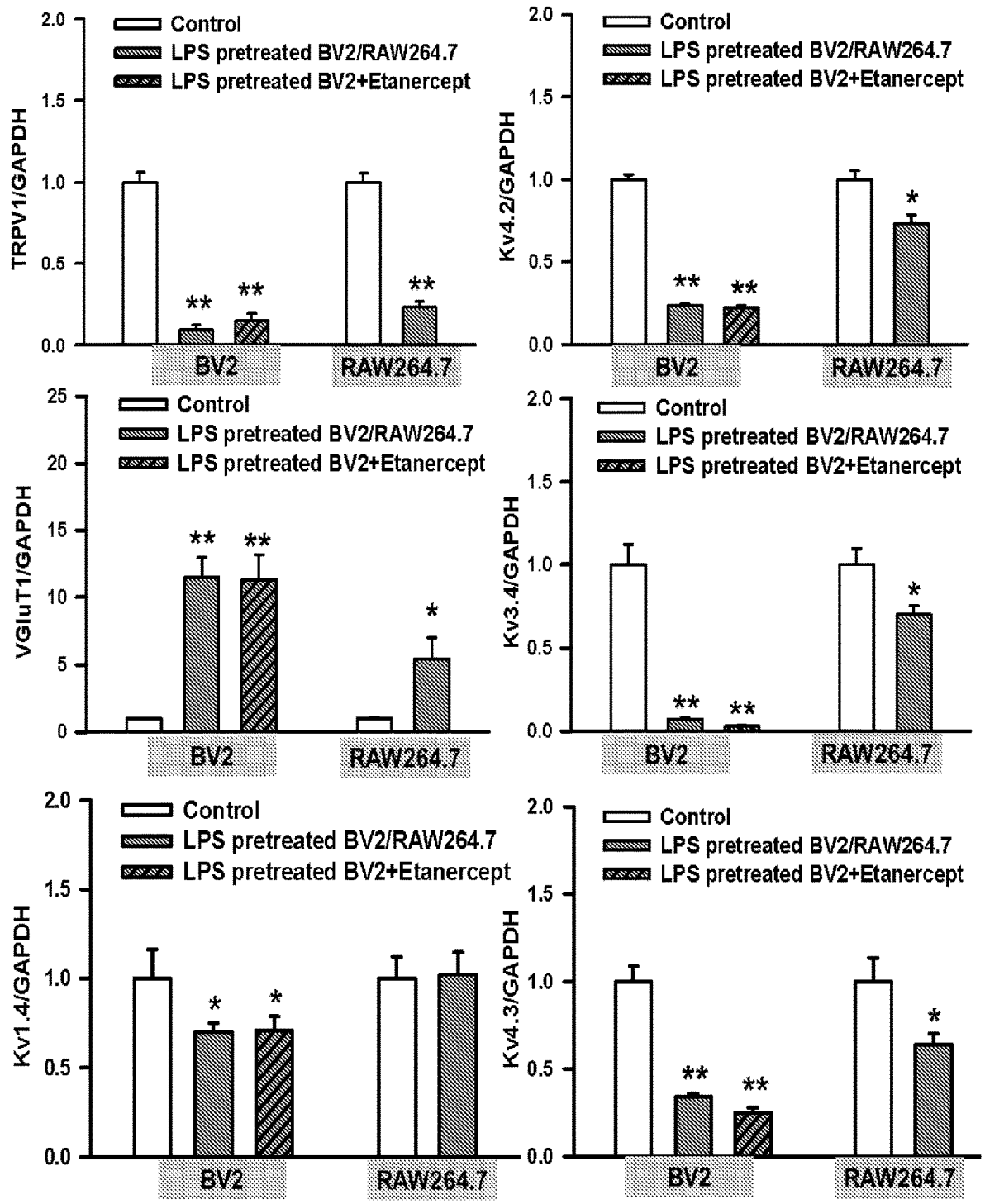

FIG. 2 provides graphs showing the protein expressions of transient receptor potential vanilloid 1 (TRPV1), vesicular glutamate transporter 1 (vGlut1) and voltage-gated potassium channels (Kv1.4, Kv4.2, Kv3.4, and Kv4.3) in 50B11 dorsal root ganglions (DRGs) either untreated (control) or exposed to i) lipopolysaccharide (LPS) treated BV2 or RAW264.7 cells or ii) LPS treated BV2 cells and etanercept. Mean±SE. n=4-6/group. *, P<0.05 and **, P<0.01 vs. Control.

Figure 3:
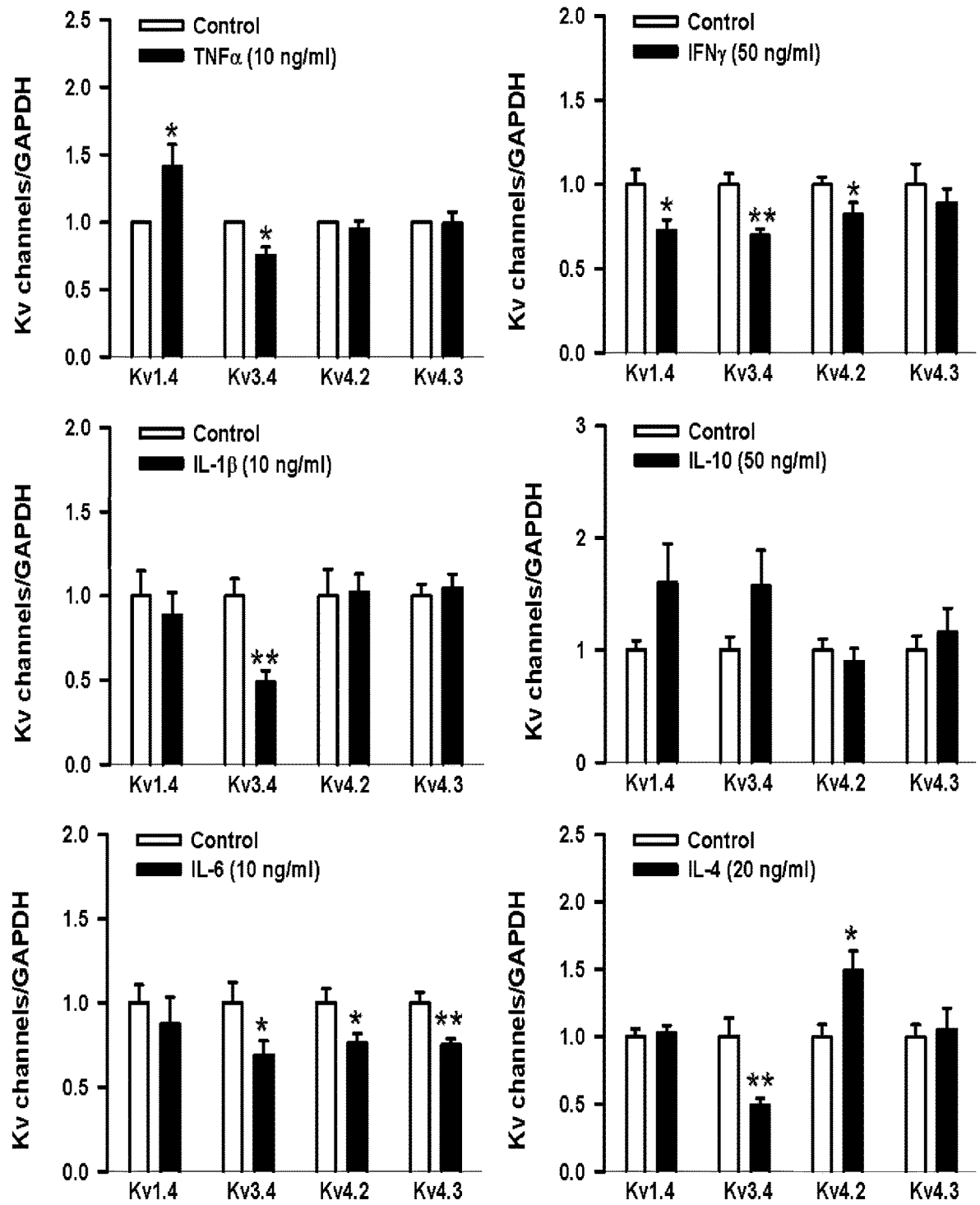

FIG. 3 provides graphs of the protein expressions of voltage-gated potassium channels (Kv1.4, Kv4.2, Kv3.4, and Kv4.3) in 50B11 DRGs either untreated (control) or treated with the indicated cytokine at the indicated concentrations. Mean±SE. n=4-6/group. *, P<0.05 vs. Control.

Figure 4:
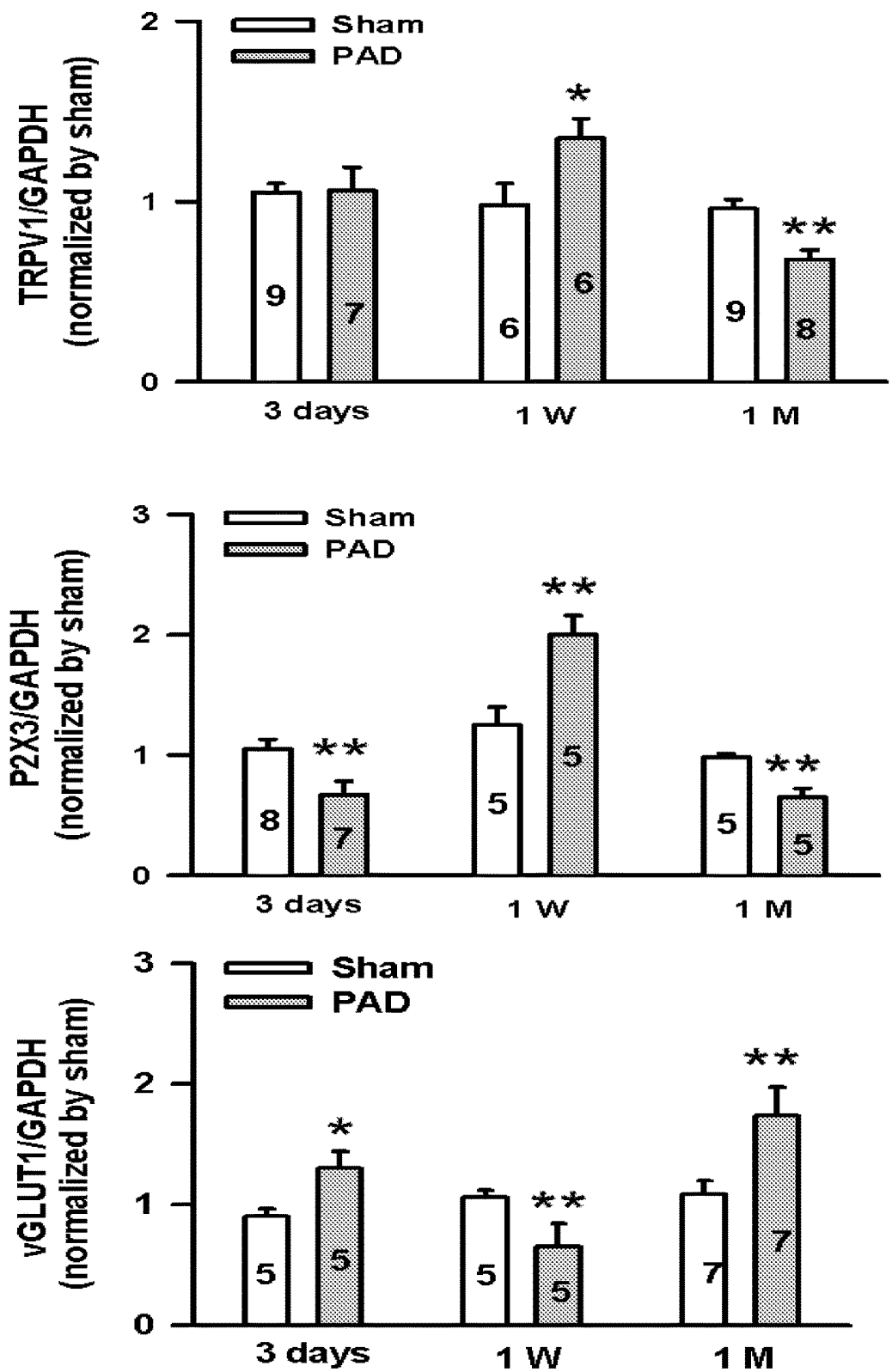

FIG. 4 provides graphs of the protein expressions of TRPV1, purinergic 2X3 (P2X3) receptor, and vGlut1 in sham treated rats (sham) or at different stages of PAD (3 days, 1 week and 1 month post PAD). Mean±SE. Number of rats indicated. * P<0.05 and ** P<0.01 vs. Sham.

Figure 5A:
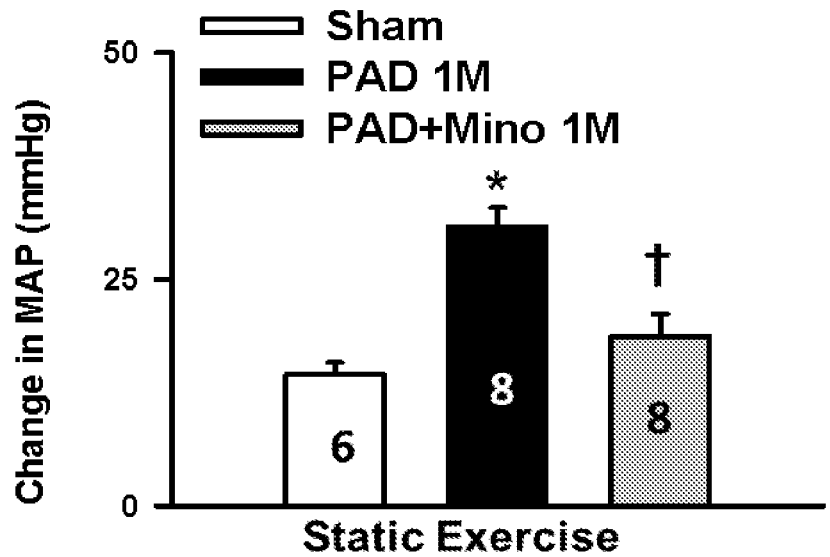
Figure 5B:
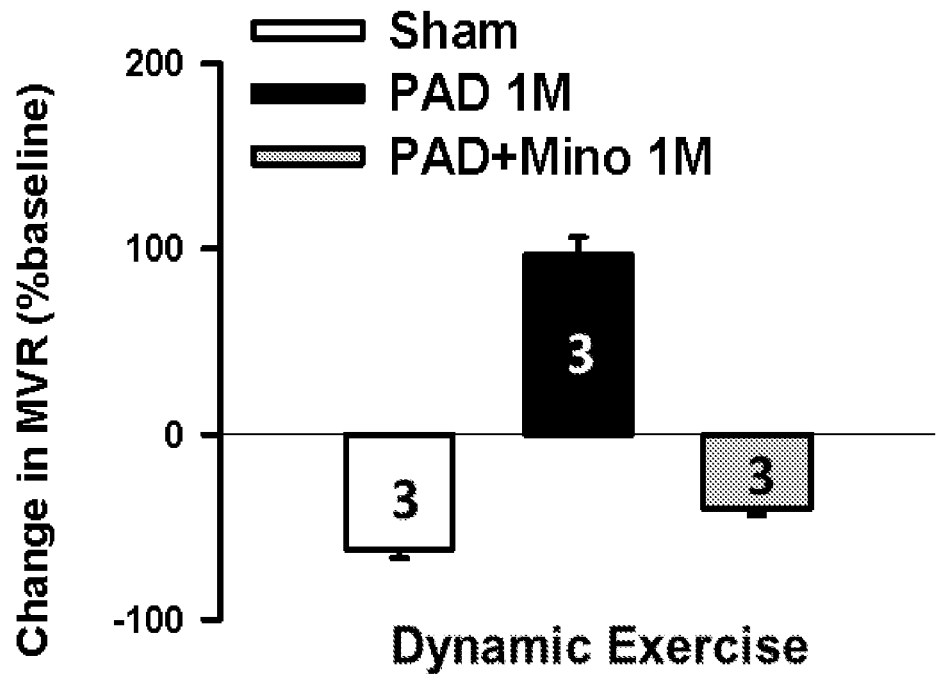

FIG. 5A provides a graph of the change in mean arterial pressure (MAP) during static exercise in sham treated rats or PAD rats at 1 month either untreated or orally treated with minocycline. Mean±SE. Number of rats indicated. * P<0.05 vs. Sham and †P<0.05 vs. PAD. FIG. 5B provides a graph of the change in microvascular resistance (MVR) during dynamic exercise in sham treated rats or PAD rats at 1 month either untreated or orally treated with minocycline. Mean±SE. Number of rats indicated.

Figure 6:
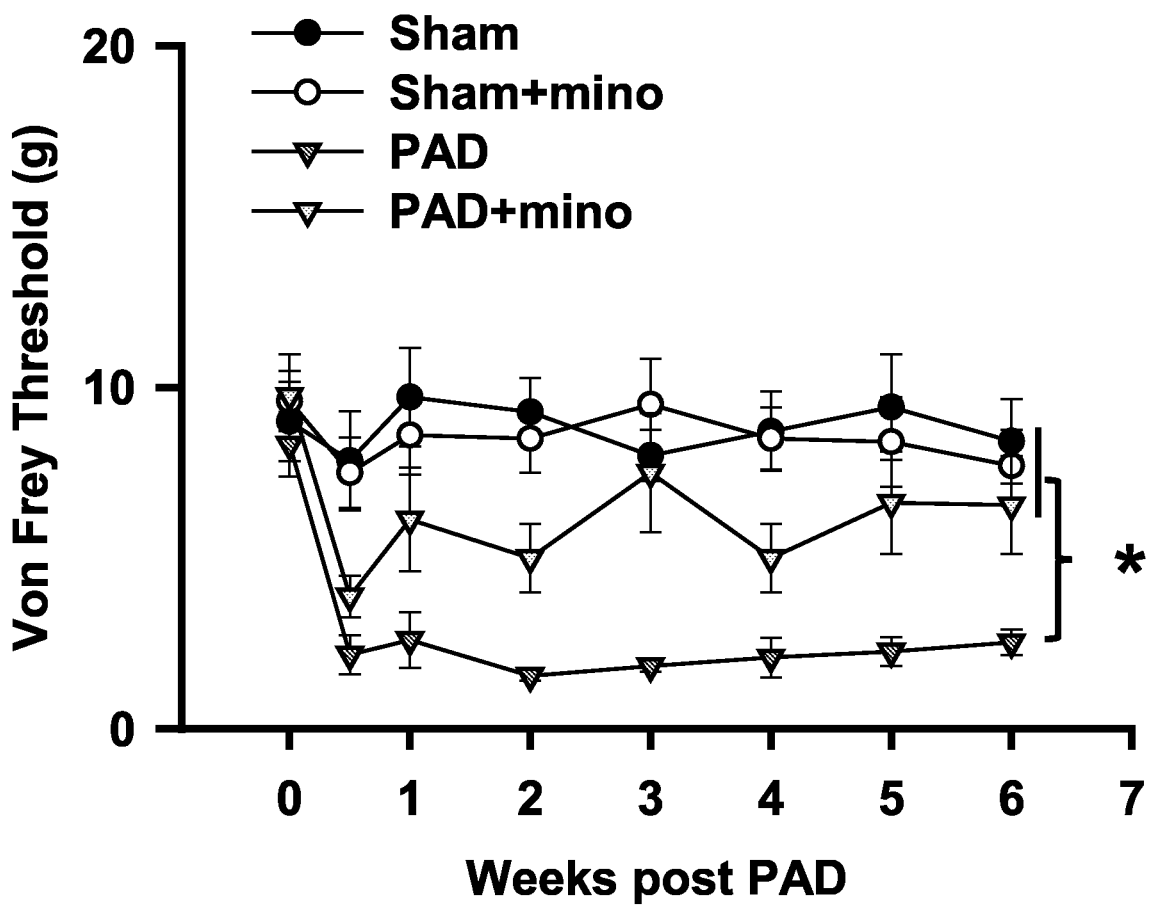

FIG. 6 provides a graph of the time-dependent Von Frey threshold in sham rats and PAD rats with and without treatment with minocycline. Mean±SE. n=6-8/group. * P<0.05 vs. PAD.

Figure 7:
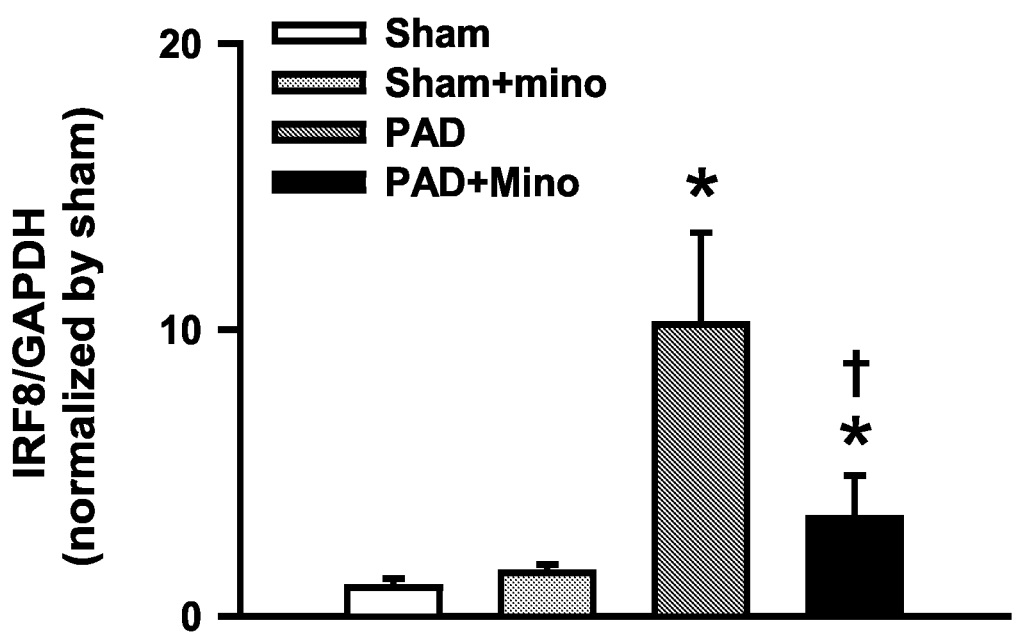

FIG. 7 provides a graph of IRF8 expression in healthy sham-treated rats or PAD rats with and without treatment with minocycline. Mean±SE. n=4-5/group. * P<0.05 vs. sham. †P<0.05 vs. PAD.

Figure 8:
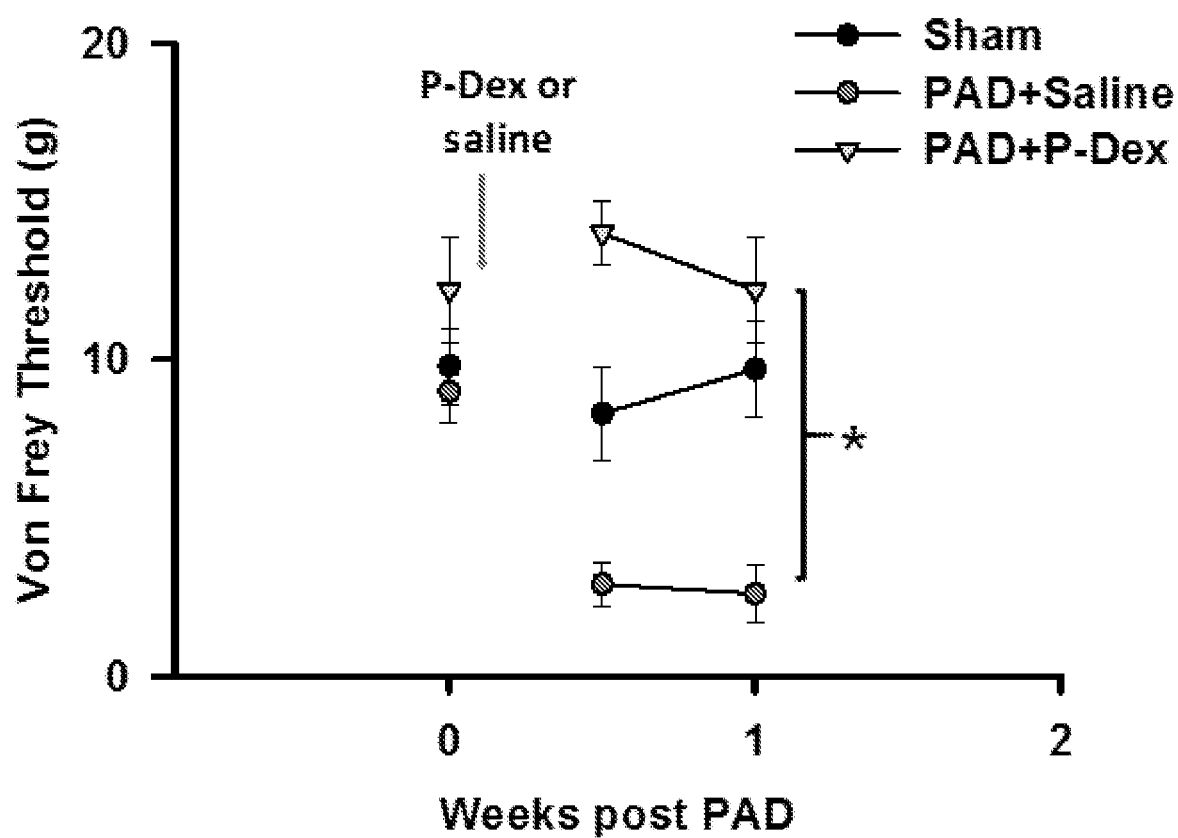

FIG. 8 provides a graph of the time-dependent Von Frey threshold in sham rats and PAD rats treated with saline or P-Dex. Mean±SE. n=5-7/group. * P<0.05 vs. PAD+saline.

Figure 9:
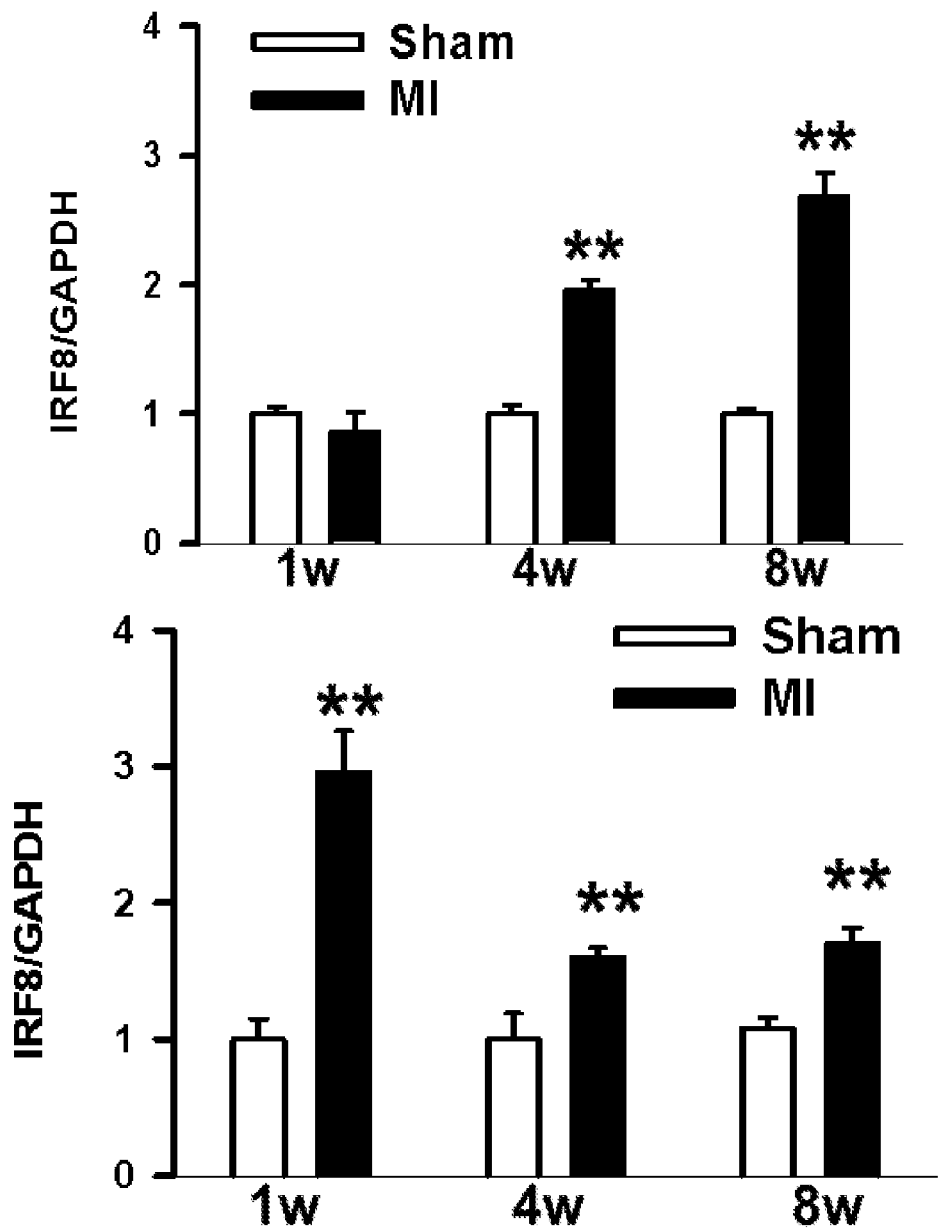

FIG. 9 provides graphs of Interferon Regulatory Factor 8 (IRF8) expression in T1-T4 DRGs (top) or stellate ganglia (bottom) of healthy sham-treated rats or MI rats at the indicated times. Mean±SE. n=4-6/each. **, P<0.01 vs. sham.

Figure 10:
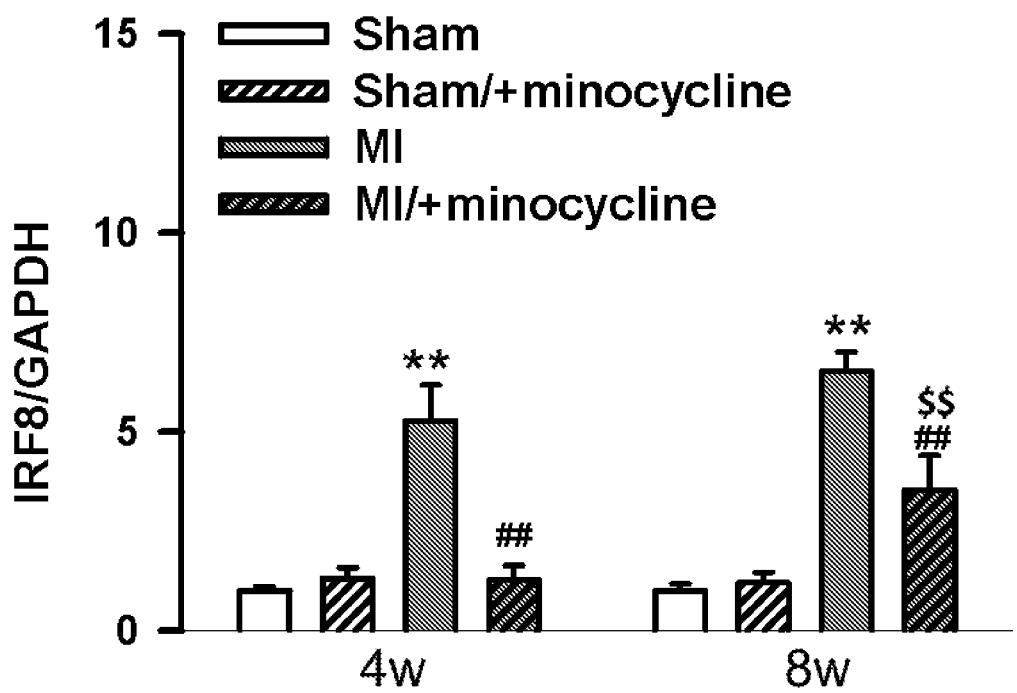

FIG. 10 provides a graph IRF8 expression in healthy sham-treated rats or MI rats with and without treatment with minocycline (20 mg/kg/day in drinking water). Mean±SE. n=4-6/group. **, P<0.01 MI+Vehicle vs. Sham+Vehicle. ##, P<0.01 MI+Minocycline vs. MI+Vehicle. $$, P<0.01 MI+Minocycline vs. Sham+Vehicle.

Figure 11:
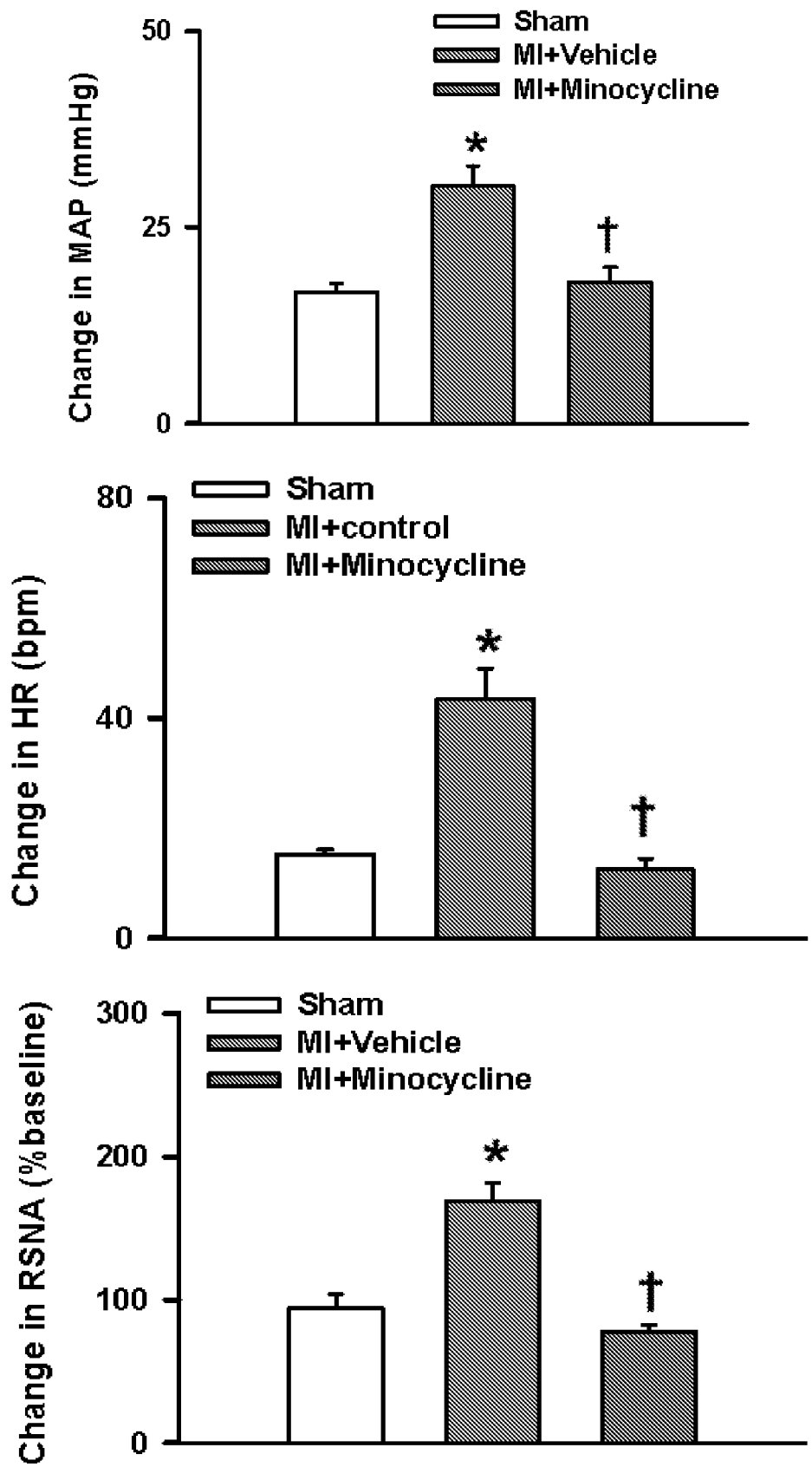

FIG. 11 provides a graph of the change in mean arterial pressure (MAP) (top), heart rate (HR) (middle), and renal sympathetic nerve activity (RSNA) (bottom) in sham treated rats or MI rats at 4 weeks either untreated (control/vehicle) or orally treated with minocycline. Mean±SE. * P<0.05 vs sham and †P<0.05 vs MI+vehicle.

Figure 12:
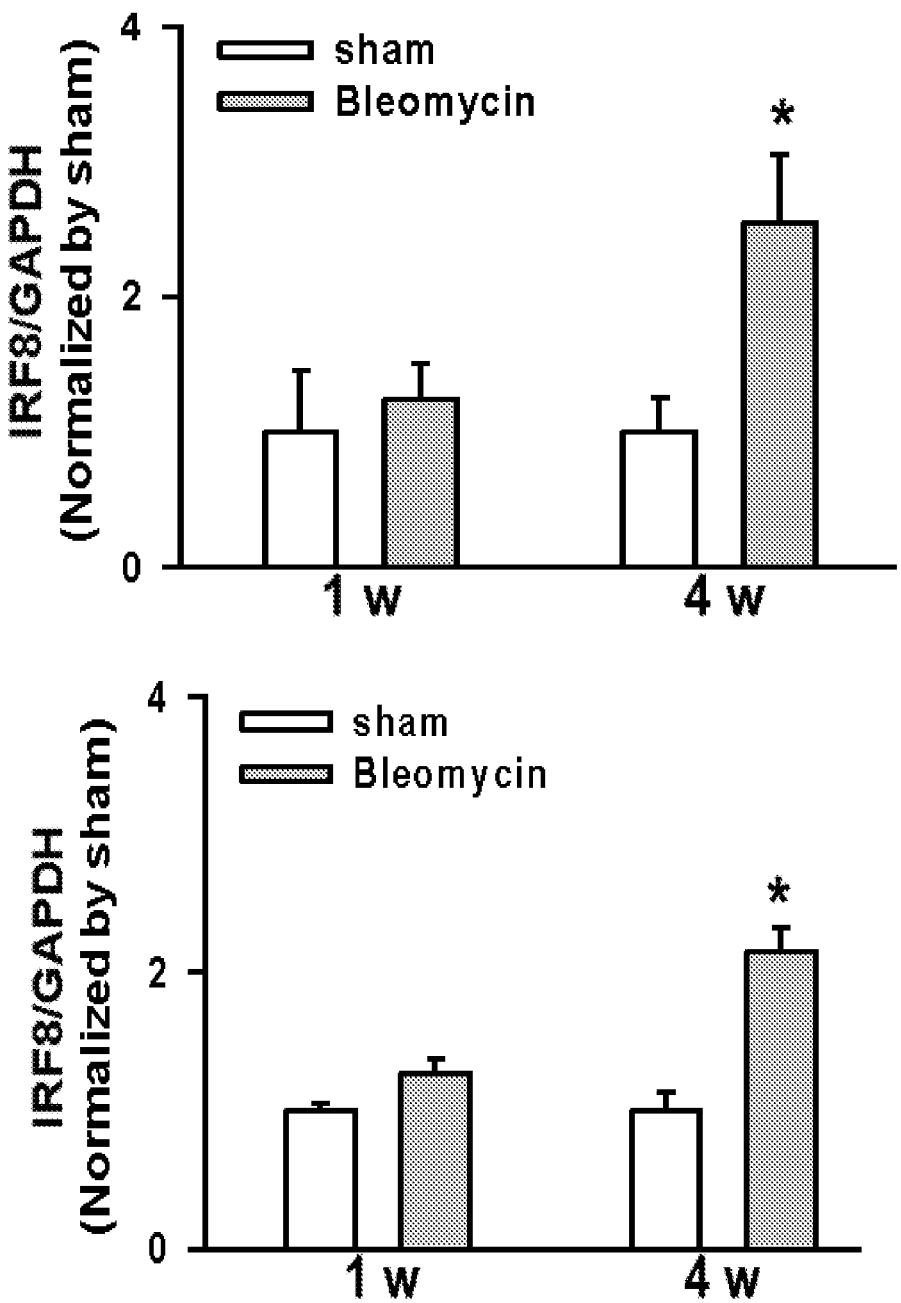

FIG. 12 provides graphs of Interferon Regulatory Factor 8 (IRF8) expression in T1-T4 DRGs (top) or stellate ganglia (bottom) of healthy sham-treated rats or bleomycin-treated rats at the indicated times. Mean±SE. n=4/each. *, P<0.05 vs. sham.

Figure 13:
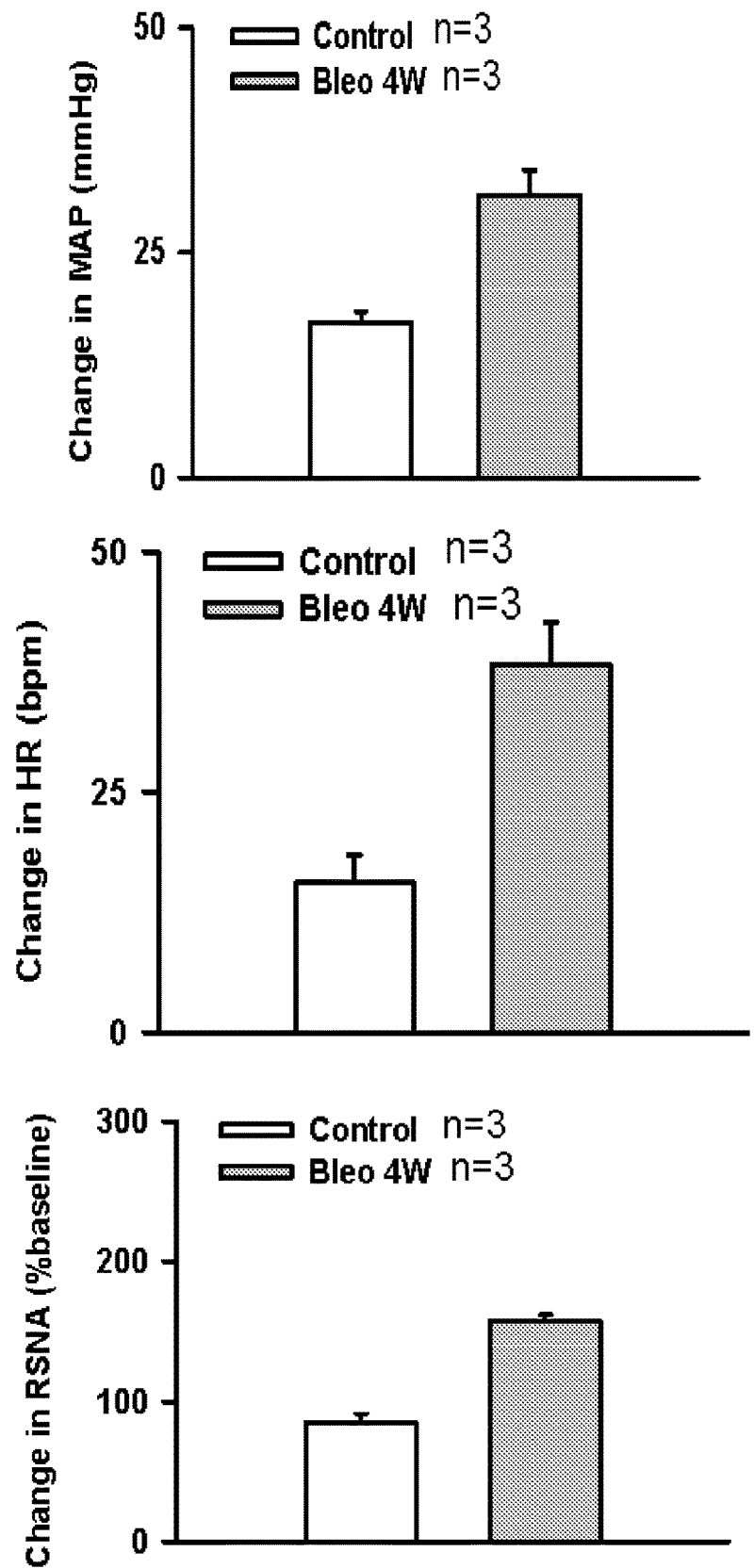

FIG. 13 provides a graph of the change in mean arterial pressure (MAP) (top), heart rate (HR) (middle), and renal sympathetic nerve activity (RSNA) (bottom) in sham treated (control) rats or bleomycin-treated rats with topical application of bradykinin (BK).

Figure 14:
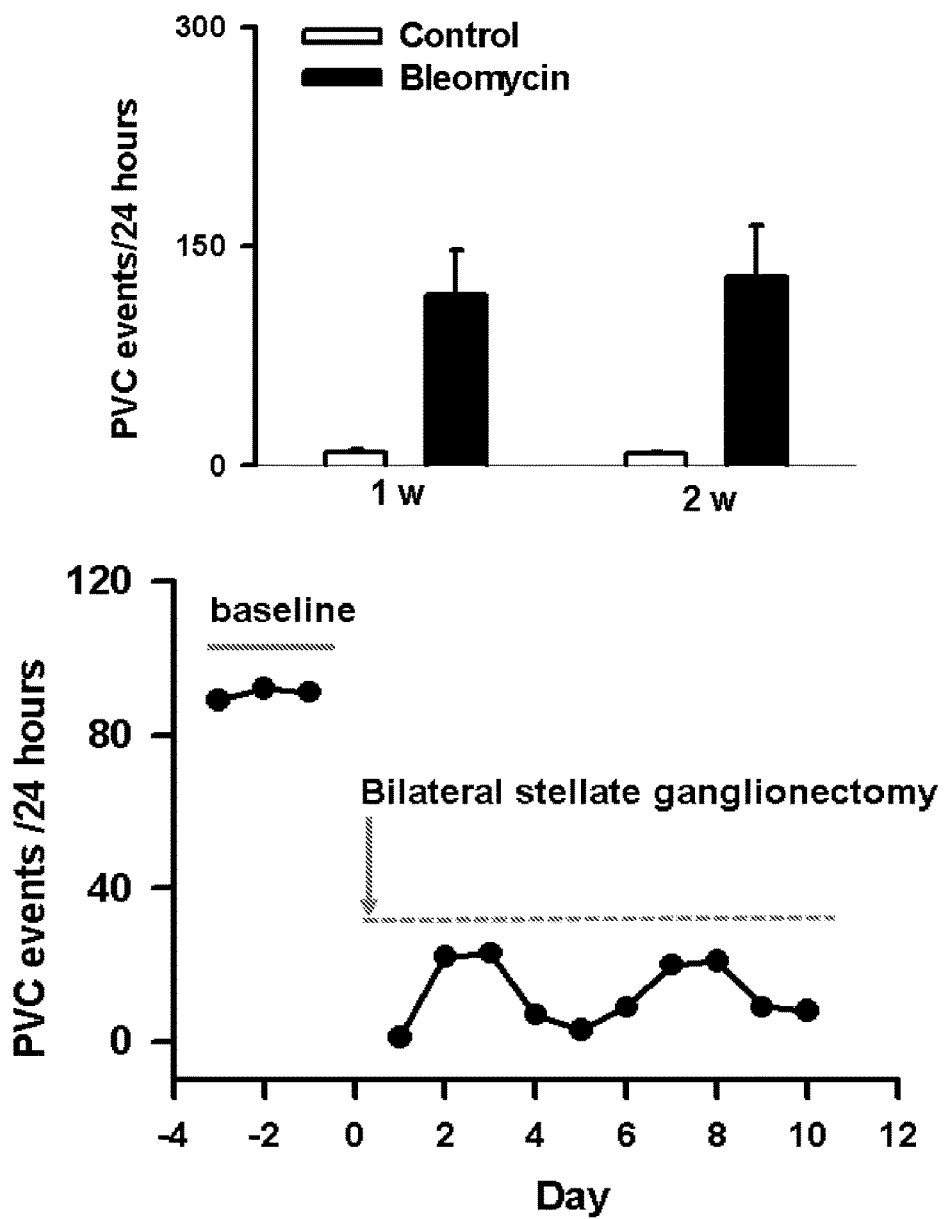

FIG. 14 provides graphs of premature ventricle contractions (PVC) per day in control rats or rats treated with a single intra-tracheal administration of bleomycin (2.5 mg/kg) at the indicated times. Mean±SE. n=3 (top) and n=2 (bottom).

DETAILED DESCRIPTION OF THE INVENTION

Atherosclerosis is the accumulation of plaques on vascular walls. The presence of atherosclerotic plaques can severely diminish vascular flow to target organs, leading to morbidity and mortality. Peripheral artery disease (PAD) occurs when atherosclerotic plaques arise in peripheral arteries, such as in the limbs, particularly the legs. Patients with PAD are at increased risk for decreased mobility, ulcers, gangrene, myocardial infarction, cerebrovascular attack, aortic aneurym rupture, and vascular death (Criqui, et al, (1997) Vasc. Med., 2:221-6; Meijer, et al. (1998) Arterioscler. Thromb. Vase Biol., 18:185-92).

One of the symptoms of PAD is claudication. Claudication is pain and/or cramping caused by too little blood flow to a subject's limbs, particularly the legs. The pain and/or cramping may occur not only during light or strenuous exercise or physical activity, but also when the subject is at rest. Contracting muscle during dynamic exercise releases many metabolites, most of which cause potent vasodilation and increase blood flow and oxygen delivery to the contracting muscles. In contrast, the exercise pressor reflex (EPR) causes increased sympathetic outflow to the muscles during exercise which limits blood flow and oxygen delivery to the contracting muscles. Without being bound by theory, the endothelium dysfunction in PAD subjects largely blunts the metabolites-induced vasodilator effect. Moreover, the ischemic-induced afferent sensitization in PAD subjects increases or exaggerates the EPR-induced vasoconstriction. Thus, the net blood flow response during exercise in PAD subjects shifts to the vasoconstriction direction, thereby causing the claudication.

Herein, it is demonstrated that chronic muscle ischemia triggers macrophage infiltration into the lumbar dorsal root ganglions (DRGs) and results in chronic sensitization of muscle afferents for both exercise intolerance and pain sensation in PAD. Therefore, macrophage activation in the lumbar DRGs is a therapeutic target to treat claudication and critical limb ischemic pain in PAD patients. It is demonstrated herein that macrophage inhibitors inhibit and/or treat PAD and related symptoms such as claudication and critical limb ischemic pain.

The instant invention encompasses methods of inhibiting, treating, and/or preventing peripheral artery disease and/or the symptoms associated therewith. In a particular embodiment, the methods inhibit, treat, and/or prevent claudication (e.g., associated with peripheral artery disease). In a particular embodiment, the methods inhibit, treat, and/or prevent limb ischemic pain (e.g., associated with peripheral artery disease), such as chronic or critical limb ischemic pain. In a particular embodiment, the methods inhibit, treat, and/or prevent muscle inflammation and/or fibrosis. In a particular embodiment, the methods improve exercise performance (e.g., ability of a subject to perform a specified exercise) and/or improve hemodynamic dysfunction in the subject (e.g., as compared to the subject before therapy). The methods comprise administering at least one agent or compound which inhibits and/or prevents macrophage activation and/or activity. In a particular embodiment, the agent or compound is a small molecule. In a particular embodiment, agent or compound inhibits and/or prevents macrophage activation. In a particular embodiment, agent or compound inhibits and/or prevents macrophage activity.

Examples of inhibitors of macrophage activation and/or activity (also referred to herein as macrophage inhibitors) include, without limitation, tetracyclines (e.g., minocycline, doxycycline, etc.), glucocorticoids (e.g., dexamethasone) or prodrugs thereof, P-Dex and analogs and/or derivatives thereof, semapimod (CNI-1493), tulathromycin, corticosteroids, auranofin, gliptins, midazolam, dasatinib, bosutinib, phosphodiesterase 4 inhibitors, and combinations thereof. In a particular embodiment, the macrophage inhibitor is minocycline. In a particular embodiment, the macrophage inhibitor is a glucocorticoid (e.g., dexamethasone). In a particular embodiment, the macrophage inhibitor is P-Dex or an analog or derivative thereof.

The macrophage inhibitors may be administered as the compound itself or as a formulation of the compound such as a prodrug or a liposome, micelle, or nanoparticle formulation. The formulations may be slow and/or fast release formulations.

P-Dex is a macromolecular prodrug of dexamethasone comprising a N-(2-hydroxypropyl)methacrylamide (HPMA) copolymer. P-Dex is described in Wang et al. (Arthritis Res. Ther. (2007) 9(1):R2, Liu et al. (Pharm Res. (2008) 25(12):2910-9), Yuan et al. (Arthritis Rheum. (2012) 64(12):4029-4039), U.S. Patent Application Publication No. 20090311182, and U.S. Pat. No. 10,092,662, each reference is incorporated by reference herein. Examples of P-Dex analogs and/or derivatives are described in U.S. Provisional Application No. 62/751,119, incorporated by reference herein. In a particular embodiment, P-Dex comprises a N-(2-hydroxypropyl)methacrylamide copolymer comprising N-(2-hydroxypropyl)methacrylamide and N-methacryloyl glycylglycyl hydrazone dexamethasone or a pharmaceutically acceptable salt thereof. The P-Dex may be a slow (sustained) or fast release prodrug. In a particular embodiment, a slow release P-Dex comprises dexamethasone linked via an acid cleavable hydrazone bond. In a particular embodiment, the P-Dex is P-Dex-slow (e.g., Liu, et al. (2008) Pharm. Res., 25:2910-2919; Quan et al. (2014) ACS Nano. 8(1):458-466). In a particular embodiment, a fast release P-Dex comprises dexamethasone linked via a hydrazone benzyl ester bond. In a particular embodiment, the P-Dex is P-Dex-fast (e.g., Krakovicova, et al. (2009) Eur. J. Pharm. Sci., 37:405-412; Quan et al. (2014) ACS Nano. 8(1):458-466).

In a particular embodiment, the macrophage inhibitor is a glucocorticoid (e.g., dexamethasone). In a particular embodiment, the glucocorticoid (e.g., dexamethasone) is in the form of a prodrug macromolecule. In a particular embodiment, the prodrug macromolecule comprises a water-soluble polymer linked (e.g., covalently) to the glucocorticoid (e.g., dexamethasone) via a cleavable bond (e.g., a pH sensitive bond (e.g., a hydrazone bond), bond cleaved by presence of a specific enzyme activity (for example, cathepsin K, MMPs, etc.), bond cleaved by changes in oxygen levels, etc.). The water-soluble polymer and glucocorticoid may be linked via a spacer. Spacers are known in the art and the person of ordinary skill in the art may select a spacer based on length, reactivity, flexibility and the like. In a particular embodiment, the spacer is an alkyl or alkyne having from one to 50 carbons, particularly one to 15 carbons. In a particular embodiment, the spacer is a peptide sequence having from one to 20, particularly one to 10 amino acids. Examples of water-soluble polymers include, without limitation, a HPMA copolymer and its derivatives, polyethylene glycol (including branched or block copolymers, which may be degradable via peptide sequences, ester or disulfide bonds, etc.), polyglutamic acid, polyaspartic acid, dextran, chitosan, cellulose and its derivatives, starch, gelatin, hyaluronic acid and its derivatives, polymer or copolymers of the following monomers: N-isopropylacrylamide, acrylamide, N,N-dimethylacrylamide, N-vinylpyrrolidone, vinyl acetate (resulting polymer hydrolyzed into polyvinyl alcohol or PVA), 2-methacryloxyethyl glucoside, acrylic acid, methacrylic, vinyl phosphonic acid, styrene sulfonic acid, maleic acid, 2-methacrylloxyethyltrimethylammonium chloride, methacrylamidopropyltrimethyl-ammonium chloride, methacryloylcholine methyl sulfate, N-methylolacrylamide, 2-hydroxy-3-methacryloxypropyltrimethyl ammonium chloride, 2-methacryloxyethyl-trimethylammonium bromide, 2-vinyl-1-methylpyridinium bromide, 4-vinyl-1-methyl-pyridinium bromide, ethyleneimine, (N-acetyl)ethyleneimine, (N-hydroxyethyl) ethyleneimine and/or allylamine. In a particular embodiment, the water-soluble polymer comprises a HPMA copolymer. In a particular embodiment, the prodrug macromolecule may comprise a targeting moiety attached (e.g., via covalent or physical bonds) to the water-soluble polymer.

In a particular embodiment, the glucocorticoid (e.g., dexamethasone) is in a liposomal formulation. In other words, the glucocorticoid (e.g., dexamethasone) is encapsulated with a liposome. In a particular embodiment, the liposome is a PEGylated liposome. In a particular embodiment, the liposome comprises polyethylene glycol $(PEG)_{2000}$-1,2-distearoyl-sn-glycero-3-phosphoethanolamine (DSPE) ($PEG_{2000}$-DSPE). In a particular embodiment, the liposome comprises $PEG_{2000}$-DSPE, dipalmitoylphosphatidylcholine (DPPC), and cholesterol. In a particular embodiment, the liposome is L-Dex (e.g., Quan et al. (2014) ACS Nano. 8(1):458-466).

In a particular embodiment, the glucocorticoid (e.g., dexamethasone) is in a micellar formulation. In other words, the glucocorticoid (e.g., dexamethasone) is within the core of a micelle. In a particular embodiment, the core of the micelle is cross-linked. In a particular embodiment, the micelle comprises poly(ethylene glycol)-b-poly(N-(2-hydroxypropyl)methacrylamide lactate). In a particular embodiment, the micelle is M-Dex (e.g., Quan et al. (2014) ACS Nano. 8(1):458-466, Crielaard et al. (2012) Angew Chem. Int. Ed. Engl., 51:7254-7258).

The methods of the instant invention may further comprise the administration (sequentially (e.g., before and/or after) and/or simultaneously) of at least one other therapeutic for the treatment of peripheral artery disease and/or a symptom thereof. For example, the methods may further comprise administering medications known to treat atherosclerosis and/or prevent heart attacks or strokes in patients with atherosclerosis. Examples of therapeutic agents that may be administered in the instant methods include, without limitation: anti-platelet agents, cholesterol-lowering drugs (e.g., statins, selective cholesterol absorption inhibitors, and resins), high blood pressure medication (e.g, diuretics, angiotensin converting enzyme (ACE) inhibitors, beta-blockers, angiotensin II receptor blockers, calcium channel blockers, alpha blockers, alpha-2 receptor agonists, central agonists, peripheral adrenergic inhibitors, and vasodilators), and antiarrythmics.

The methods of the instant invention may further comprise diagnosing peripheral artery disease in the subject prior to administration of the therapeutic agents of the instant invention. For example, PAD may be diagnosed by the ankle-brachial index. Briefly, the blood pressure is taken at an upper extremity (e.g., the arm) and at a lower extremity (e.g., the foot or ankle) and then the ratio of the systolic pressure in the lower extremity to that in the upper extremity is calculated. If the ratio is less than 0.90, PAD is diagnosed. Generally, the lower the ratio, the more severe the disease. For example, severe arterial narrowing is diagnosed when the ratio is less than about 0.50. In a particular embodiment, the subject being treated by the methods of the instant invention has an ankle-brachial index ratio less than 0.9, less than 0.8, less than 0.7, less than 0.6, or less than 0.5.

The instant invention also encompasses compositions, particularly for inhibiting, treating, and/or preventing peripheral artery disease and/or the symptoms (e.g., claudication and/or limb ischemic pain) associated therewith. The compositions comprise i) at least one at least one macrophage inhibitor such as minocycline, and ii) at least one pharmaceutically acceptable carrier. In a particular embodiment, the composition further comprises at least one other therapeutic agent for the treatment of the peripheral artery disease and/or a symptom thereof, as described above.

The therapeutic agents of the present invention can be administered by any suitable route, for example, by injection (e.g., for local, direct, or systemic administration), oral, pulmonary, topical, nasal or other modes of administration. The therapeutic agents may be contained within a composition with at least one pharmaceutically acceptable carrier. The therapeutic agents may be administered by any suitable means including, for example: by injection or by parenteral, intramuscular, intravenous, intraarterial, intraperitoneal, subcutaneous, oral, topical, inhalatory, transdermal, intrapulmonary, intraareterial, intrarectal, intramuscular, intranasal, intrathecal, epidural, intraganglionic, and intra-spinal administration. In a particular embodiment, the composition is administered by oral administration, intravenous injection, intrathecal administration, epidural administration, intra-DRG administration, or intraganglionic administration. In a particular embodiment, the therapeutic agents are administered via intraganglionic administration such as intra-dorsal root ganglia (DRG), intra/peri-stellate ganglia, and intra- or peri-nodose ganglia. In a particular embodiment, the therapeutic agents are administered to the nodose ganglia. In a particular embodiment, the therapeutic agents are administered via within the lumbar dorsal root ganglions (DRGs) (e.g., by an epidural injection). In a particular embodiment, the intra-DRG injection is made at one or more of the lumbar regions L1-L6, particularly L4-L6. In a particular embodiment, the intra-DRG injection is at L4 and/or L5.

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), antioxidants (e.g., ascorbic acid, sodium metabisulfite), preservatives (e.g., Thimersol, benzyl alcohol) and bulking substances (e.g., lactose, mannitol). Common carriers include, without limitation, water, oil, buffered saline, ethanol, polyol (for example, glycerol, propylene glycol, liquid polyethylene glycol and the like), dimethyl sulfoxide (DMSO), detergents, suspending agents, glucose, lactose, gum acacia, gelatin, mannitol, starch paste, magnesium trisilicate, talc, corn starch, keratin, colloidal silica, potato starch, urea, medium chain length triglycerides, dextrans, other carriers suitable for use in manufacturing preparations, in solid, semisolid, or liquid form, and suitable mixtures thereof. In addition, excipients and auxiliary, stabilizing, preserving, thickening, flavoring, and coloring agents may be included in the compositions. The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington's Pharmaceutical Sciences and Remington: The Science and Practice of Pharmacy). The pharmaceutical composition of the present invention can be prepared, for example, in liquid form, or can be in dried powder form (e.g., lyophilized for later reconstitution).

The therapeutic agents described herein will generally be administered to a subject/patient as a pharmaceutical preparation. The term "patient" as used herein refers to human or animal subjects. The compositions of the instant invention may be employed therapeutically or prophylactically, under the guidance of a physician. The compositions comprising the agent of the instant invention may be conveniently formulated for administration with any pharmaceutically acceptable carrier(s). The concentration of agent in the chosen medium may be varied and the medium may be chosen based on the desired route of administration of the pharmaceutical preparation. Except insofar as any conventional media or agent is incompatible with the agent to be administered, its use in the pharmaceutical preparation is contemplated. In a particular embodiment, the pharmaceutical compositions are formulated for intra-DRG injections.

The dose and dosage regimen of the therapeutic agent according to the invention that is suitable for administration to a particular patient may be determined by a physician considering the patient's age, sex, weight, general medical condition, and the specific condition for which the agent is being administered to be treated or prevented and the severity thereof. The physician may also take into account the route of administration, the pharmaceutical carrier, and the agent's biological activity. Selection of a suitable pharmaceutical preparation will also depend upon the mode of administration chosen.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment or prevention therapy. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation or prevention of a particular condition may be determined by dosage concentration curve calculations, as known in the art.

The pharmaceutical preparation comprising the therapeutic agent may be administered at appropriate intervals until the pathological symptoms are reduced or alleviated, after which the dosage may be reduced to a maintenance level. The appropriate interval in a particular case would normally depend on the condition of the patient.

Toxicity and efficacy (e.g., therapeutic, preventative) of the particular formulas described herein can be determined by standard pharmaceutical procedures such as, without limitation, in vitro, in cell cultures, ex vivo, or on experimental animals. The data obtained from these studies can be used in formulating a range of dosage for use in human. The dosage may vary depending upon form and route of administration. Dosage amount and interval may be adjusted individually to levels of the active ingredient which are sufficient to deliver a therapeutically or prophylactically effective amount.

In accordance with another aspect of the instant invention, methods of inhibiting, treating, and/or preventing a cardiopulmonary disease or disorder, acute or chronic heart or lung injury, and/or associated symptoms including, without limitation, arrhythmia, heart failure, myocardial infarction, pulmonary dysfunction, and cardiac dysfunction. Examples of cardiopulmonary disease or disorders include, without limitation, myocardial infarction, cardiac arrhythmias, congestive heart failure, chronic heart failure, coronary heart disease, atherosclerosis, dysrhythmias, cardiomyothopy, cardiac arrest, bronchitis, asthma, chronic obstructive pulmonary disease, cystic fibrosis, emphysema, pulmonary fibrosis (e.g., idiopathic pulmonary fibrosis), pneumonia, pulmonary hypertension. In a particular embodiment, the methods inhibit, treat, and/or prevent an acute heart injury. In a particular embodiment, the methods inhibit, treat, and/or prevent a myocardial infarction. In a particular embodiment, the methods inhibit, treat, and/or prevent pulmonary fibrosis. The methods comprise administering at least one agent or compound which inhibits and/or prevents macrophage activation and/or activity. In a particular embodiment, the agent or compound is a small molecule. In a particular embodiment, agent or compound inhibits and/or prevents macrophage activation. In a particular embodiment, agent or compound inhibits and/or prevents macrophage activity.

Examples of inhibitors of macrophage activation and/or activity (also referred to herein as macrophage inhibitors) include, without limitation, tetracyclines (e.g., minocycline, doxycycline, etc.), glucocorticoids (e.g., dexamethasone) or prodrugs thereof, P-Dex and analogs and/or derivatives thereof, semapimod (CNI-1493), tulathromycin, corticosteroids, auranofin, gliptins, midazolam, dasatinib, bosutinib, phosphodiesterase 4 inhibitors, and combinations thereof. In a particular embodiment, the macrophage inhibitor is minocycline. In a particular embodiment, the macrophage inhibitor is a glucocorticoid (e.g., dexamethasone). In a particular embodiment, the macrophage inhibitor is P-Dex or an analog or derivative thereof.

The macrophage inhibitors may be administered as the compound itself or as a formulation of the compound such as a prodrug or a liposome, micelle, or nanoparticle formulation. The formulations may be slow and/or fast release formulations.

P-Dex is a macromolecular prodrug of dexamethasone comprising a N-(2-hydroxypropyl)methacrylamide (HPMA) copolymer. P-Dex is described in Wang et al. (Arthritis Res. Ther. (2007) 9(1):R2, Liu et al. (Pharm Res. (2008) 25(12):2910-9), Yuan et al. (Arthritis Rheum. (2012) 64(12):4029-4039), U.S. Patent Application Publication No. 20090311182, and U.S. Pat. No. 10,092,662, each reference is incorporated by reference herein. Examples of P-Dex analogs and/or derivatives are described in U.S. Provisional Application No. 62/751,119, incorporated by reference herein. In a particular embodiment, P-Dex comprises a N-(2-hydroxypropyl)methacrylamide copolymer comprising N-(2-hydroxypropyl)methacrylamide and N-methacryloyl glycylglycyl hydrazone dexamethasone or a pharmaceutically acceptable salt thereof. The P-Dex may be a slow (sustained) or fast release prodrug. In a particular embodiment, a slow release P-Dex comprises dexamethasone linked via an acid cleavable hydrazone bond. In a particular embodiment, the P-Dex is P-Dex-slow (e.g., Liu, et al. (2008) Pharm. Res., 25:2910-2919; Quan et al. (2014) ACS Nano. 8(1):458-466). In a particular embodiment, a fast release P-Dex comprises dexamethasone linked via a hydrazone benzyl ester bond. In a particular embodiment, the P-Dex is P-Dex-fast (e.g., Krakovicova, et al. (2009) Eur. J. Pharm. Sci., 37:405-412; Quan et al. (2014) ACS Nano. 8(1):458-466).

In a particular embodiment, the macrophage inhibitor is a glucocorticoid (e.g., dexamethasone). In a particular embodiment, the glucocorticoid (e.g., dexamethasone) is in the form of a prodrug macromolecule. In a particular embodiment, the prodrug macromolecule comprises a water-soluble polymer linked (e.g., covalently) to the glucocorticoid (e.g., dexamethasone) via a cleavable bond (e.g., a pH sensitive bond (e.g., a hydrazone bond), bond cleaved by presence of a specific enzyme activity (for example, cathepsin K, MMPs, etc.), bond cleaved by changes in oxygen levels, etc.). The water-soluble polymer and glucocorticoid may be linked via a spacer. Spacers are known in the art and the person of ordinary skill in the art may select a spacer based on length, reactivity, flexibility and the like. In a particular embodiment, the spacer is an alkyl or alkyne having from one to 50 carbons, particularly one to 15 carbons. In a particular embodiment, the spacer is a peptide sequence having from one to 20, particularly one to 10 amino acids. Examples of water-soluble polymers include, without limitation, a HPMA copolymer and its derivatives, polyethylene glycol (including branched or block copolymers, which may be degradable via peptide sequences, ester or disulfide bonds, etc.), polyglutamic acid, polyaspartic acid, dextran, chitosan, cellulose and its derivatives, starch, gelatin, hyaluronic acid and its derivatives, polymer or copolymers of the following monomers: N-isopropylacrylamide, acrylamide, N,N-dimethylacrylamide, N-vinylpyrrolidone, vinyl acetate (resulting polymer hydrolyzed into polyvinyl alcohol or PVA), 2-methacryloxyethyl glucoside, acrylic acid, methacrylic, vinyl phosphonic acid, styrene sulfonic acid, maleic acid, 2-methacrylloxyethyltrimethylammonium chloride, methacrylamidopropyltrimethyl-ammonium chloride, methacryloylcholine methyl sulfate, N-methylolacrylamide, 2-hydroxy-3-methacryloxypropyltrimethyl ammonium chloride, 2-methacryloxyethyl-trimethylammonium bromide, 2-vinyl-1-methylpyridinium bromide, 4-vinyl-1-methyl-pyridinium bromide, ethyleneimine, (N-acetyl)ethyleneimine, (N-hydroxyethyl) ethyleneimine and/or allylamine. In a particular embodiment, the water-soluble polymer comprises a HPMA copolymer. In a particular embodiment, the prodrug macromolecule may comprise a targeting moiety attached (e.g., via covalent or physical bonds) to the water-soluble polymer.

In a particular embodiment, the glucocorticoid (e.g., dexamethasone) is in a liposomal formulation. In other words, the glucocorticoid (e.g., dexamethasone) is encapsulated with a liposome. In a particular embodiment, the liposome is a PEGylated liposome. In a particular embodiment, the liposome comprises polyethylene glycol $(PEG)_{2000}$-1,2-distearoyl-sn-glycero-3-phosphoethanolamine (DSPE) ($PEG_{2000}$-DSPE). In a particular embodiment, the liposome comprises $PEG_{2000}$-DSPE, dipalmitoylphosphatidylcholine (DPPC), and cholesterol. In a particular embodiment, the liposome is L-Dex (e.g., Quan et al. (2014) ACS Nano. 8(1):458-466).

In a particular embodiment, the glucocorticoid (e.g., dexamethasone) is in a micellar formulation. In other words, the glucocorticoid (e.g., dexamethasone) is within the core of a micelle. In a particular embodiment, the core of the micelle is cross-linked. In a particular embodiment, the micelle comprises poly(ethylene glycol)-b-poly(N-(2-hydroxypropyl)methacrylamide lactate). In a particular embodiment, the micelle is M-Dex (e.g., Quan et al. (2014) ACS Nano. 8(1):458-466, Crielaard et al. (2012) Angew Chem. Int. Ed. Engl., 51:7254-7258).

The methods of the instant invention may further comprise the administration (sequentially (e.g., before and/or after) and/or simultaneously) of at least one other therapeutic for the treatment of a cardiopulmonary disease or disorder, acute or chronic heart or lung injury, and/or associated symptoms. For example, the methods may further comprise administering medications known to treat atherosclerosis and/or prevent heart attacks or strokes in patients with atherosclerosis. Examples of therapeutic agents that may be administered in the instant methods include, without limitation: anti-platelet agents, cholesterol-lowering drugs (e.g., statins, selective cholesterol absorption inhibitors, and resins), high blood pressure medication (e.g, diuretics, angiotensin converting enzyme (ACE) inhibitors, beta-blockers, angiotensin II receptor blockers, calcium channel blockers, alpha blockers, alpha-2 receptor agonists, central agonists, peripheral adrenergic inhibitors, and vasodilators), and anti-arrythmics.

The methods of the instant invention may further comprise diagnosing a cardiopulmonary disease or disorder and/or an acute or chronic heart or lung injury in the subject prior to administration of the therapeutic agents of the instant invention.

The instant invention also encompasses compositions, particularly for inhibiting, treating, and/or preventing a cardiopulmonary disease or disorder, acute or chronic heart or lung injury, and/or associated symptoms. The compositions comprise i) at least one at least one macrophage inhibitor such as minocycline, and ii) at least one pharmaceutically acceptable carrier. In a particular embodiment, the composition further comprises at least one other therapeutic agent for the treatment of a cardiopulmonary disease or disorder, acute or chronic heart or lung injury, and/or associated symptoms, as described above.

The therapeutic agents of the present invention can be administered by any suitable route, for example, by injection (e.g., for local, direct, or systemic administration), oral, pulmonary, topical, nasal or other modes of administration. The therapeutic agents may be contained within a composition with at least one pharmaceutically acceptable carrier. The therapeutic agents may be administered by any suitable means including, for example: by injection or by parenteral, intramuscular, intravenous, intraarterial, intraperitoneal, subcutaneous, oral, topical, inhalatory, transdermal, intrapulmonary, intraareterial, intrarectal, intramuscular, intranasal, intrathecal, epidural, intraganglionic, and intra-spinal administration. In a particular embodiment, the composition is administered by oral administration, intravenous injection, intrathecal administration, epidural administration, intra-DRG administration, intra-stellate ganglia administration, or intraganglionic administration. In a particular embodiment, the therapeutic agents are administered via intraganglionic administration such as intra-dorsal root ganglia (DRG), intra/peri-stellate ganglia, and intra- or peri-nodose ganglia. In a particular embodiment, the therapeutic agents are administrated to the nodose ganglia. In a particular embodiment, the therapeutic agents are administered within the thoracic dorsal root ganglions (DRGs) (e.g., by an epidural injection). In a particular embodiment, the intra-DRG injection is made at one or more of the thoracic regions T1-T4. In a particular embodiment, the therapeutic agents are administered to the stellate ganglia.

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), antioxidants (e.g., ascorbic acid, sodium metabisulfite), preservatives (e.g., Thimersol, benzyl alcohol) and bulking substances (e.g., lactose, mannitol). Common carriers include, without limitation, water, oil, buffered saline, ethanol, polyol (for example, glycerol, propylene glycol, liquid polyethylene glycol and the like), dimethyl sulfoxide (DMSO), detergents, suspending agents, glucose, lactose, gum acacia, gelatin, mannitol, starch paste, magnesium trisilicate, talc, corn starch, keratin, colloidal silica, potato starch, urea, medium chain length triglycerides, dextrans, other carriers suitable for use in manufacturing preparations, in solid, semisolid, or liquid form, and suitable mixtures thereof. In addition, excipients and auxiliary, stabilizing, preserving, thickening, flavoring, and coloring agents may be included in the compositions. The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention (see, e.g., Remington's Pharmaceutical Sciences and Remington: The Science and Practice of Pharmacy). The pharmaceutical composition of the present invention can be prepared, for example, in liquid form, or can be in dried powder form (e.g., lyophilized for later reconstitution).

The therapeutic agents described herein will generally be administered to a subject/patient as a pharmaceutical preparation. The term "patient" as used herein refers to human or animal subjects. The compositions of the instant invention may be employed therapeutically or prophylactically, under the guidance of a physician. The compositions comprising the agent of the instant invention may be conveniently formulated for administration with any pharmaceutically acceptable carrier(s). The concentration of agent in the chosen medium may be varied and the medium may be chosen based on the desired route of administration of the pharmaceutical preparation. Except insofar as any conventional media or agent is incompatible with the agent to be administered, its use in the pharmaceutical preparation is contemplated. In a particular embodiment, the pharmaceutical compositions are formulated for intra-DRG injections and/or intra-stellate injections.

The dose and dosage regimen of the therapeutic agent according to the invention that is suitable for administration to a particular patient may be determined by a physician considering the patient's age, sex, weight, general medical condition, and the specific condition for which the agent is being administered to be treated or prevented and the severity thereof. The physician may also take into account the route of administration, the pharmaceutical carrier, and the agent's biological activity. Selection of a suitable pharmaceutical preparation will also depend upon the mode of administration chosen.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment or prevention therapy. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation or prevention of a particular condition may be determined by dosage concentration curve calculations, as known in the art.

The pharmaceutical preparation comprising the therapeutic agent may be administered at appropriate intervals until the pathological symptoms are reduced or alleviated, after which the dosage may be reduced to a maintenance level. The appropriate interval in a particular case would normally depend on the condition of the patient.

Toxicity and efficacy (e.g., therapeutic, preventative) of the particular formulas described herein can be determined by standard pharmaceutical procedures such as, without limitation, in vitro, in cell cultures, ex vivo, or on experimental animals. The data obtained from these studies can be used in formulating a range of dosage for use in human. The dosage may vary depending upon form and route of administration. Dosage amount and interval may be adjusted individually to levels of the active ingredient which are sufficient to deliver a therapeutically or prophylactically effective amount.

DEFINITIONS

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition or symptom resulting in a decrease in the probability that the subject will develop the condition or symptom.

A "therapeutically effective amount" of a compound or a pharmaceutical composition refers to an amount effective to prevent, inhibit, treat, or lessen the symptoms of a particular disorder or disease. The treatment of peripheral artery disease herein may refer to curing, relieving, and/or preventing peripheral artery disease, the symptom(s) of it, or the predisposition towards it.

As used herein, the term "subject" refers to an animal, particularly a mammal, particularly a human.

As used herein, "diagnose" refers to detecting and identifying a disease or disorder in a subject. The term may also encompass assessing or evaluating the disease or disorder status (severity, progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality). In other words, the term "prognosis" refers to providing a prediction of the probable course and outcome of a disease/disorder or the likelihood of recovery from the disease/disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "exercise performance" refers to physical acts or exertion which typically dependent on skeletal muscle contraction. Examples of exercise performance include, without limitation, running (e.g., speed and/or endurance), walking (e.g., speed and/or endurance), swimming (e.g., speed and/ or endurance), and lifting (e.g., strength and/or endurance).

The following examples describe illustrative methods of practicing the instant invention and are not intended to limit the scope of the invention in any way.

EXAMPLE 1

Muscle afferent sensitization is a key event to mediate the pathogenesis of claudication in the PAD state. In the normal condition, muscle afferents can be activated below the pain threshold to regulate cardiovascular and respiratory systems during physical activity via the exercise pressor reflex (EPR), a neural reflex originating in skeletal muscle. The EPR-evoked vasoconstriction in exercising PAD muscle is exaggerated, which further decreases the blood flow to the exercising muscles of the PAD leg (which are already limited by atherosclerotic blockages), leading to activation of muscle afferents above the nociceptive threshold level and producing the familiar exertional pain symptoms of claudication. However, the molecular mechanisms underlying the muscle afferent sensitization in the chronic PAD state was unclear.

Herein, it is demonstrated that chronic muscle ischemia triggers macrophage infiltration into the lumbar dorsal root ganglions (DRGs) and results in chronic sensitization of muscle afferents for both exercise intolerance and pain sensation in PAD. Therefore, macrophage activation in the lumbar DRGs is a therapeutic target to treat claudication and critical limb ischemic pain in PAD patients. Macrophage inhibitors (e.g., minocycline, dexamethasone, and P-Dex) can be used to treat PAD and related symptoms such as claudication and critical limb ischemic pain.

A PAD rat model was utilized. Briefly, the PAD rat model is a created by femoral artery occlusion. Catheter-based femoral artery occlusion was created by placing a modified PE50 catheter (its cavity filled with solid agarose) between common iliac artery and left femoral artery to interrupt hindlimb blood supply. The whole procedure is similar to the telemetry implant surgery. Generally, rats were anesthetized using a 2%-3% isoflurane:oxygen mixture. A warm water blanket was used to provide intra-operative heat support to prevent hypothermia. Rats were placed in the prone position and the surgical site (i.e., the femoral area) was cleared of hair, prepared with iodine or chlorhexidine, and the femoral artery was exposed. After a small incision was made, a modified PE50 catheter was placed into the femoral artery and advanced about 3.5 cm to the iliac artery at the aortic bifurcation. The distal end of the femoral artery was ligated with 4-0 Dexon suture. The skin was closed with external interrupted 4-0 or 3-0 prolene suture, which were removed in 10-14 days after the surgery.

Immunohistochemistry studies demonstrated the time-dependent macrophage infiltration and activation in lumbar DRGs after femoral arterial occlusion. Briefly, rats (sham treated of PAD model) were anesthetized with pentobarbital sodium (40 mg/kg, i.p.). The rats were perfused with 4% paraformaldehyde (PFA) and the L4-L6 DRGs were immediately dissected and post-fixed in 4% PFA overnight. Sections were cut using a cryostat after dehydration with 30% sucrose. After being treated with 10% donkey serum (Jackson ImmumoResearch, West Grove, PA) for 60 minutes, sections were incubated with anti-neurofilament 200 (NF200) antibody (an A-fiber neuron marker; Finkel, T. (1998) Curr. Opin. Cell Biol., 10:248-253)), isolectin B4 (IB4) antibody (a C-fiber neuron marker; Wang, et al. (1994) Neuroscience 62:539-551), and anti-ionized calcium-binding adapter molecule 1 (IBA1) antibody. After being washed with PBS, sections were coverslipped with Aqua-Mount Mounting Medium (VWR Corp., Radnor, PA) and were examined with a laser confocal microscope (Model TSC STED; Leica, Buffalo Grove, IL). IBA1 is found on activated macrophages whereas (IB4) is a marker for peripheral neurons with unmyelinated fibers and NF200 is a marker for neurons with myelinated fibers. The immunofluorescence results demonstrated increasing numbers of IBA1 positive cells (indicating activated macrophage) in PAD rats over the timecourse of 3 days, 1 week, and 1 month among the neurons (IB4 or NF200 positive cells) of the lumbar DRGs.

To quantitate the infiltrating and activated macrophage, a Western blot analysis was performed on the rat samples with anti-Interferon Regulatory Factor 8 (IRF8) antibodies. IRF8 is a transcriptional regulator that plays critical roles in the activation of macrophages by proinflammatory signals such as interferon-γ (IFN-γ). The expression of IRF8 was normalized to glyceraldehyde 3-phosphate dehydrogenase (GAPDH). As seen in FIG. 1, IRF8 expression increased in PAD rats but not sham rats, indicating the infiltration and activation of macrophage into lumbar DRGs.

It was then investigated how activated macrophage influence DRG. Briefly, RAW264.7 macrophage or BV2 microglial cells were seeded in a permeable cell culture insert and treated with lipopolysaccharide (LPS) for 4 hours. BV2 cells were optionally treated with etanercept (tumor necrosis factor (TNF) inhibitor) as well. The LPS was then washed out by replacement with fresh media. The culture insert was moved into a new transwell containing DRG neurons (50B11 DRG neurons) and maintained for 24 hours. The culture insert was replaced with a new one containing fresh LPS-treated BV2 or RAW264.7 cells every 24 hours for 3 days. DRGs were then harvested. Western blot analyses were performed for determining the effect of chronic macrophage activation on the protein expressions of transient receptor potential vanilloid 1 (TRPV1; a ligand-gated non-selective cation channel), vesicular glutamate transporter 1 (vGlut1; vesicle-bound, sodium-dependent phosphate transporter), and voltage-gated potassium channels (Kv1.4, Kv4.2, Kv3.4, and Kv4.3) in DRGs. FIG. 2 shows the expression of the indicated proteins normalized to GAPDH, thereby demonstrating the effect of chronic macrophage activation on protein expression.

The effect of individual proinflammatory and anti-inflammatory cytokines on the protein expressions of voltage-gated potassium channels in the 50B11 DRG cell line was then investigated. Specifically, DRGs were incubated with a proinflammatory cytokine—TNFα (10 ng/ml), IL-1β (10 ng/ml), IL-6 (10 ng/ml), or IFNγ (50 ng/ml)—or an anti-inflammatory cytokine—IL-10 (50 ng/ml) or IL-4 (20 ng/ml). Western blot analyses were performed to determine the effect of individual cytokines on the protein expressions of voltage-gated potassium channels (Kv1.4, Kv4.2, Kv3.4, and Kv4.3) in DRGs. FIG. 3 shows the expression of the indicated proteins normalized to GAPDH, thereby demonstrating the effect of individual cytokines on protein expression. Notably, individual cytokines have a differential effect on DRG neurons. Thus, anti-inflammatory therapy targeting a single cytokine would be insufficient. However, the targeting of macrophage activation would be more effective because activated macrophages are the donor of many cytokines.

The time-dependent protein expression of TRPV1, purinergic 2X3 receptor (P2X3), and vGlut1 was investigated in the PAD rat model. Specifically, the protein expression was measured at 3 days, 1 week and 1 month post PAD. P2X3 receptor channels expressed in sensory neurons are activated by extracellular ATP, serve important roles in nociception and sensory hypersensitization, and participates in pathways controlling macrophage activation. As seen in FIG. 4, expression of TRPV1 is decreased 1 month post PAD while expression of vGlut1 is increased 1 month post PAD, compared to controls. P2X3 receptor expression first increased 1 week post PAD and then decreased by one month post PAD.

Exercise Pressor Reflex (EPR) is exaggerated in the chronic PAD state, which causes an exaggerated vasoconstriction in excising muscle during dynamic exercise. The pressor and tachycardia responses in sham treated rats or PAD rats to static exercise or dynamic exercise muscle were measured. The responses in PAD rats given oral minocycline (20 mg/kg/day) started 3 days before femoral arterial occlusion were also measured. Briefly, PowerLab (Model 16S) and LabChart software (version 7.0) (ADInstruments, Colorado Springs, CO) were used to obtain arterial blood pressure (ABP), mean arterial pressure (MAP), heart rate (HR), microvascular resistance (MVR), and muscle tension. The peak response from each was determined by the difference of the greatest change from the baseline value. Baseline values were calculated by averaging 30 seconds of data before the muscle contraction. Tension-time index was calculated by integration of the area between the tension trace and the baseline level expressed in kg×s. The change in MAP and MVR are shown in FIGS. 5A and 5B, respectively. Significantly, oral minocycline started 3 day before femoral arterial occlusion prevented the development of the exaggerated EPR as well as vasoconstriction in excising muscle during dynamic exercise in chronic PAD rats.

It was then determined whether minocycline could prevent the development of mechanical allodynia in chronic PAD rats. Allodynia refers to central pain sensitization following normally non-painful, often repetitive, stimulation. In other words, allodynia can lead to pain from stimuli which do not normally provoke pain. To this end, a Von Frey assay was used. The Von Frey assay uses small pieces of nylon rod to test a rodent's sensitivity to a mechanical stimulus. As seen in FIG. 6, oral minocycline (20 mg/kg/ day) started 3 day before femoral arterial occlusion prevents the development of mechanical allodynia in chronic PAD rats.

It was then determined whether minocycline could prevent the macrophage activation in lumbar DRGs of chronic PAD rats. As seen in FIG. 7, IRF8 expression was dramatically decreased in PAD rats treated with oral minocycline (20 mg/kg/day) started 3 day before femoral arterial occlusion compared to PAD rats, indicating the inhibition of the infiltration and activation of macrophage into lumbar DRGs.

In order to demonstrate that the effects with minocycline were observed with other macrophage inhibitors, PAD rats were treated with a one-time bolus intravenous (IV) injection of P-Dex (80 mg/kg) started 10 minutes after femoral arterial occlusion. As seen in FIG. 8, the administration of P-Dex prevents the development of mechanical allodynia post PAD as determined by the Von Frey assay.

EXAMPLE 2

Pulmonary and cardiovascular diseases are leading causes of morbidity and mortality worldwide. Many lung diseases are often associated with cardiovascular complications, and vice versa. The heart and lungs work in synergy to provide oxygen to the organism in normal physiological conditions. The interaction between these two organs becomes even more profound during cardiopulmonary disease. For example, up to 30% of patients admitted to hospital for community-acquired pneumonia (which leads to 1.1 million hospital admissions in the United States annually and 60,000 deaths) develop cardiovascular complications such as myocardial infarctions, cardiac arrhythmias and heart failure, acutely and up to 10 years thereafter. Patients with chronic obstructive pulmonary disease (COPD) or lung resection surgery also have high incidence of cardiac arrhythmias including atrial fibrillation and ventricular arrhythmias. On the other hand, patients with chronic cardiac diseases are often associated with pulmonary dysfunction. These clinical phenomena highlight the importance of understanding the cardio-pulmonary interaction in the management of patients with cardiopulmonary diseases.

Previous interests in the cardiopulmonary critical care field had been heavily focused on the mechanical interaction between the two organs. However, little attention has been given to a potential cardiopulmonary neural interaction. Data is provided herein which indicates that damage to one organ (either heart or lung) will trigger a neuro-inflammatory cascade that includes macrophage activation in autonomic ganglia common to both organs. This results in both sensory (e.g., thoracic T1-T4 DRGs) and autonomic (e.g., stellate ganglia) dysfunction in the cardiopulmonary system, both of which contributes to cardiac comorbidity in these diseases.

The data provided herein shows that macrophage infiltration (e.g., neural inflammation) in the peripheral nervous system including thoracic DRGs and stellate ganglia after either heart or lung injury is pro-sympatho-excitatory and pro-arrhythmogenic. This event is a novel therapeutic target to treat cardiovascular comorbidity (e.g., cardiac arrhythmia) following cardiac or lung injury. Therefore, delivery, particularly local delivery, of one or more therapeutic agents that inhibit macrophage activation and/or activity can treat, inhibit, and/or prevent either heart or lung injury-induced cardiac comorbidity.

Notably, there is no available clinical therapeutic approach to target macrophage activation in thoracic T1-T4 DRGs and stellate ganglia in cardiovascular diseases. Thus, the instant invention is a completely new therapeutic concept. Stellate ganglia block, whose primary component is anesthetics such as 2% lidocaine or bupivacaine, has been offered to treat cardiac arrhythmia. However, this block lasts for a very short period (1-2 days). One fundamental difference between intra-stellate injection of anti-macrophage agents and stellate ganglia block is that the former targets at the glial cells around the stellate ganglia neurons whereas the latter targets at the neurons themselves. However, due to the short-life of anesthetics, direct neuronal inhibitory effect by stellate ganglia block cannot last very long. Once the anesthetics effect withdraws, arrhythmia will come back again. On the other hand, suppression of macrophage activation in stellate ganglia, which removes the external stimuli (i.e. macrophage) to the stellate ganglia neurons, will calm down these neurons. Anti-macrophage agents such as P-Dex can maintain their effect for more than one month in stellate ganglia. Accordingly, a much longer anti-arrhythmia effect can be obtained with the instant invention compared to traditional stellate ganglia blockage. Similar benefits can be achieved when these drugs are applied into thoracic T1-T4 DRGs.

Myocardial infarction (MI) was produced in rats by ligating the left coronary artery. A sham group was created in a similar fashion without coronary artery ligation. In brief, rats were anesthetized with 3% isoflurane and ventilated at 60 breaths/minute. A left-sided thoracotomy was created level with the fifth intercostal space. The pericardium was opened, the heart was exteriorized, and the left anterior descending coronary artery ligated near its origin. All sham rats survived, but there was a ~30% mortality in the rats that were subject to coronary artery ligation.

Immunohistochemistry studies demonstrated the time-dependent macrophage infiltration and activation into T1-T4 DRGs and stellate ganglia after myocardial infarction. Briefly, rats (sham treated of MI model) were anesthetized with pentobarbital sodium (40 mg/kg, i.p.). The rats were perfused with 4% paraformaldehyde (PFA) and the T4-T6 DRGs were immediately dissected and post-fixed in 4% PFA overnight. Sections were cut using a cryostat after dehydration with 30% sucrose. After being treated with 10% donkey serum (Jackson ImmunoResearch, West Grove, PA) for 60 minutes, sections were incubated with anti-neurofilament 200 (NF200) antibody (an A-fiber neuron marker; Finkel, T. (1998) Curr. Opin. Cell Biol., 10:248-253)), isolectin B4 (IB4) antibody (a C-fiber neuron marker; Wang, et al. (1994) Neuroscience 62:539-551), anti-ionized calcium-binding adapter molecule 1 (IBA1) antibody, tyrosine hydroxylase (TH; a dopaminergic neuron marker for sympathetic ganglia). After being washed with PBS, sections were coverslipped with Aqua-Mount Mounting Medium (VWR Corp., Radnor, PA) and were examined with a laser confocal microscope (Model TSC STED; Leica, Buffalo Grove, IL). IBA1 is found on activated macrophages whereas (IB4) is a marker for peripheral neurons with unmyelinated fibers and NF200 is a marker for neurons with myelinated fibers. The immunofluorescence images demonstrating a time-dependent increase in IBA1-immunoreactive cells in T1-T4 DRGs and stellate ganglia in post-myocardial infarction rats over the timecourse of 1 week, 4 weeks, and 8 weeks. Very few IBA1-immunoreactive cells were observed in sham treated samples.

To quantitate the infiltrating and activated macrophage, a Western blot analysis was performed on the rat samples with anti-Interferon Regulatory Factor 8 (IRF8) antibodies. IRF8 is a pro-inflammatory M1 macrophage/microglia marker. The expression of IRF8 was normalized to glyceraldehyde 3-phosphate dehydrogenase (GAPDH). The data provided in FIG. 9 clearly show the time-dependent macrophage activation in both T1-T4 DRGs and stellate ganglia post myocardial infarction.

An RNA sequence analysis was performed which showed that mRNA expression of interferon regulatory factor 7 (IRF7, a key transcription factor converting anti-inflammatory M2 macrophages into pro-inflammatory M1 macrophages) was significantly upregulated (fold change (CHF/sham): 1.60, P=1.03E-05) in T1-T4 DRGs in chronic heart failure (CHF) rats 8-weeks post-MI (n=5) compared to healthy sham (n=4). Upregulated mRNA expression of several other inflammatory genes such as RGD1309362 (fold change (CHF/sham): 1.85, P=1.11E-05), slfn4 (fold change (CHF/sham): 1.58, P=2.60E-08) and lfit1 (fold change (CHF/sham): 3.57, P=4.91E-07) was also observed.

As explained above in Example 1, activated macrophage influence DRG (FIG. 2). Indeed, the presence of activated macrophage effected the expression of transient receptor potential vanilloid 1 (TRPV1; a ligand-gated non-selective cation channel), vesicular glutamate transporter 1 (vGlut1; vesicle-bound, sodium-dependent phosphate transporter), and voltage-gated potassium channels (Kv1.4, Kv4.2, Kv3.4, and Kv4.3) in DRGs.

As also explained in Example 1, individual proinflammatory and anti-inflammatory cytokines effect the protein expressions of voltage-gated potassium channels in the DRGs (FIG. 3). Notably, individual cytokines have a differential effect on DRG neurons. Thus, anti-inflammatory therapy targeting a single cytokine would be insufficient. However, the targeting of macrophage activation would be more effective because activated macrophages are the donor of many cytokines.

It was then determined whether minocycline could prevent the macrophage activation in DRGs of MI rats. As seen in FIG. 10, chronic administration of minocycline (20 mg/kg/day in drinking water) can completely prevent the upregulated macrophage activation marker IRF8 in the T1-T4 DRGs until 4 weeks post MI and still largely suppress the macrophage activation at 8 weeks post MI.

For measuring vitals of the rats, a Millar catheter (SPR 524; size, 3.5-Fr; Millar Instruments, Houston, TX) was advanced through the right common carotid artery and progressed into the aorta and left in place to record arterial pressure (AP), mean arterial pressure (MAP), and heart rate (HR), using PowerLab (Model 16S) and LabChart software (version 7.0) (ADInstruments, Colorado Springs, CO). Renal sympathetic nerve activity (RSNA) and integrated RSNA (iRSNA) were also measured. RSNA was recorded as described (Gao, et al. (2005) Hypertension 45:1173-1181; Wang, et al. (2010) J. Appl. Physiol., 108:1365-1375; Becker, et al. (2016) J. Physiol., 594:5711-5725). In brief, the left kidney, renal artery, and nerves were exposed through a left retroperitoneal flank incision. Sympathetic nerves running on or beside the renal artery were identified. The renal sympathetic nerves were placed on a pair of platinum-iridium recording electrodes and cut distally to avoid recording afferent activity. Nerve activity was amplified (910,000) and filtered (bandwidth: 100 to 3000 Hz) using a Grass P55C preamplifier. The nerve signal was displayed on a computer where it was rectified, integrated, sampled (1 KHz), and converted to a digital signal by the Power-Lab data acquisition system. At the end of the experiment, the rat was euthanized with an overdose of pentobarbital sodium. Respective noise levels were subtracted from the nerve recording data before percent changes from baseline were calculated. Integrated RSNA (iRSNA) was normalized as 100% of mean baseline during the control period (Becker, et al. (2016) J. Physiol., 594:5711-5725). As seen in FIG. 11, a 4-week continuous treatment with minocycline (20 mg/kg/day) via drinking water completely abolished the exaggerated cardiovascular response to epicardial application of bradykinin (BK, 10 µg/ml) in the post-MI rats in the 4 weeks post-MI rats. Topical application of BK causes an exaggerated pressor and sympatho-excitatory response in vagotomized rats after 4-week MI compared to sham, which can be observed by increases in HR, MAP, and RSNA.

Immunohistochemistry studies demonstrated the time-dependent macrophage infiltration and activation into T1-T4 DRGs and stellate ganglia after lung injury caused by bleomycin administration. Bleomycin induces experimental lung fibrosis in a variety of animal models and it causes inflammatory and fibrotic reactions within a short period of time, even more so after intratracheal instillation. As seen in FIG. 12, IRF8 protein expression increases in both T1-T4 DRGs and stellate ganglia in 4-weeks post-bleomycin rats. Further, as seen in FIG. 13, activation of cardiac spinal afferents by topical application of BK (10 µg/ml) caused an exaggerated pressor and sympatho-excitatory response in vagotomized rats 4-weeks after bleomycin (Bleo) compared to sham. In addition, FIG. 14 shows that a single intratracheal delivery of bleomycin (2.5 mg/kg) causes a dramatic increase in premature ventricle contractions (PVC) in rats, which can be almost completely abolished by bilateral stellate ganglionectomy.

Based on the above data, heart or lung injury-induced cardiac comorbidity can be treated via delivery (e.g., local delivery) of a macrophage inhibitor such as, without limitation, minocycline, dexamethasone, or P-Dex to thoracic DRGs and/or stellate ganglia.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. A method for inhibiting or treating peripheral artery disease and/or associated symptoms in a subject, said method comprising administering an inhibitor of macrophage activation and/or activity to said subject,
    wherein said inhibitor is administered via intra- or peri-ganglion injection, intra-dorsal root ganglion (DRG) injection, or epidural injection.

2. The method of claim 1, wherein said inhibitor is administered via intra- or peri-ganglion injection- or intra-dorsal root ganglion (DRG) injection.

3. The method of claim 2, wherein said inhibitor is administered via intra-DRG injection.

4. The method of claim 3, wherein the intra-DRG injection is at one or more of the lumbar regions L4-L6.

5. The method of claim 1, wherein said inhibitor is administered via injection within the lumbar dorsal root ganglion.

6. The method of claim 1, wherein said inhibitor is selected from the group consisting of minocycline, a tetracycline, glucocorticoid, dexamethasone, P-Dex, semapimod (CNI-1493), tulathromycin, corticosteroids, auranofin, gliptins, midazolam, dasatinib, bosutinib, phosphodiesterase 4 inhibitors, and combinations thereof.

7. The method of claim 1, wherein said method inhibits or treats claudication associated with said peripheral artery disease, improves the exercise performance of the subject, and/or inhibits or treats limb ischemic pain associated with said peripheral artery disease.

8. The method of claim 1, further comprising administration of at least one other therapeutic for the treatment of peripheral artery disease and/or a symptom thereof.

9. The method of claim 8, wherein said other therapeutic is selected from the group consisting of anti-platelet agents, cholesterol-lowering drugs, high blood pressure medication, and antiarrhythmics.

10. The method of claim 1, further comprising diagnosing peripheral artery disease in the subject prior to administration of said inhibitor.

11. The method of claim 1, wherein said inhibitor is a prodrug or formulated within a liposome, micelle, or nanoparticle.

12. The method of claim 1, wherein said inhibitor is administered via injection within the lumbar dorsal root ganglion, and wherein said inhibitor is a tetracycline or a glucocorticoid.

13. A method for inhibiting or treating cardiopulmonary diseases, acute or chronic heart or lung injury, and/or associated symptoms in a subject, said method comprising administering an inhibitor of macrophage activation and/or activity to said subject,
wherein said inhibitor is administered via intra- or peri-ganglion injection, intra-dorsal root ganglion (DRG) injection, epidural injection, or intra-stellate ganglia injection.

14. The method of claim 13, wherein said inhibitor is administered via intra- or peri-ganglion injection, intra-dorsal root ganglion (DRG) injection, or intra-stellate ganglia injection.

15. The method of claim 14, wherein said inhibitor is administered via intra-DRG injection, via intra- or peri-stellate ganglia injection, or via injection within the thoracic dorsal root ganglion.

16. The method of claim 15, wherein the intra-DRG injection is at one or more of the thoracic regions T1-T4.

17. The method of claim 13, wherein said inhibitor is selected from the group consisting of minocycline, a tetracycline, glucocorticoid, dexamethasone, P-Dex, semapimod (CNI-1493), tulathromycin, corticosteroids, auranofin, gliptins, midazolam, dasatinib, bosutinib, phosphodiesterase 4 inhibitors, and combinations thereof.

18. The method of claim 13, wherein said cardiopulmonary diseases, acute or chronic heart or lung injury, and/or associated symptoms is selected from the group consisting of arrhythmia, heart failure, myocardial infarction, pulmonary dysfunction, and cardiac dysfunction.

19. The method of claim 13, further comprising administration of at least one other therapeutic for the treatment of cardiopulmonary diseases, acute or chronic heart or lung injury, and/or associated symptoms.

20. The method of claim 19, wherein said other therapeutic is selected from the group consisting of anti-platelet agents, cholesterol-lowering drugs, high blood pressure medication, and antiarrhythmics.

21. The method of claim 13, further comprising diagnosing a cardiopulmonary disease or acute or chronic heart or lung injury in the subject prior to administration of said inhibitor.

22. The method of claim 13, wherein said inhibitor is a prodrug or formulated within a liposome, micelle, or nanoparticle.

23. The method of claim 13, wherein said inhibitor is administered via injection within the thoracic dorsal root ganglion or stellate ganglia, and wherein said inhibitor is a tetracycline.

* * * * *